(12) United States Patent
Brehm et al.

(10) Patent No.: US 10,507,545 B2
(45) Date of Patent: Dec. 17, 2019

(54) LASER ABLATION MACHINE FOR LABELING CRYOGENICALLY-FROZEN VIALS

(71) Applicant: MERIAL INC., Duluth, GA (US)

(72) Inventors: Andy Brehm, Jefferson, GA (US); Dennis Jerome Freeman, Cleveland, GA (US); Ed Schindler, Snellville, GA (US); Julie Campbell, Baldwin, GA (US)

(73) Assignee: BOEHRINGER INGELHEIM ANIMAL HEALTH USA INC., Duluth ( * ) Notice: Subject to any disclaimer, the term of this patent is extended or adjusted under 35 U.S.C. 154(b) by 237 days.

(21) Appl. No.: 15/499,127

(22) Filed: Apr. 27, 2017

(65) Prior Publication Data

US 2017/0312852 A1 Nov. 2, 2017

Related U.S. Application Data

(60) Provisional application No. 62/330,071, filed on Apr. 30, 2016.

(51) Int. Cl.
 *B41M 5/26* (2006.01)
 *B23K 26/362* (2014.01)
 (Continued)

(52) U.S. Cl.
 CPC .......... *B23K 26/127* (2013.01); *A01N 1/0236* (2013.01); *A01N 1/0257* (2013.01);
 (Continued)

(58) Field of Classification Search
 CPC .. B23K 26/127; B23K 26/361; B23K 26/362; B23K 28/00; B23K 37/047; A01N 1/0268; A01N 1/0257; A01N 1/0236; B41M 5/24
 See application file for complete search history.

(56) References Cited

U.S. PATENT DOCUMENTS 6,818,859 B2 11/2004 Lodge
7,647,867 B2 1/2010 Byron
(Continued)

FOREIGN PATENT DOCUMENTS

CA      2966200      * 5/2016 .............. B41M 5/24
KR   20170078763   * 7/2017 .............. B41M 5/24
(Continued)

OTHER PUBLICATIONS

U.S. Appl. No. 15/498,933, Not yet published, Merial, Inc.

*Primary Examiner* — Huan H Tran
(74) *Attorney, Agent, or Firm* — Judy Jarecki-Black; John Ezcurra

(57) ABSTRACT

The invention relates to a machine for labeling "blank-labeled" cryogenically-frozen vials or ampoules, which contain heat-labile biological materials, and to which a laser-light sensitive material had been applied prior to freezing. Accordingly, the machine has been designed to maintain the integrity of the biological materials throughout all phases of the labeling process. The machine generally comprises a master control system; a programmable user interface; a frame; cryogenic freezer assemblies, for keeping the vials at the required low temperatures; an infeed assembly, configured to receive and position blank-labeled cryogenic vials; a cryostatic labeling/quality control tunnel, wherein the vials are maintained at the required temperature, labeled by laser ablation, and checked for quality; and, an outfeed assembly. The machine further comprises a means for transporting the vials from the infeed assembly to the tunnel, and from the tunnel to the outfeed assembly. Vials labeled according to the instant disclosure are ultimately manually or automatically loaded into cryogenic shipping containers.

19 Claims, 18 Drawing Sheets

(51) Int. Cl.
*B41M 5/24* (2006.01)
*B23K 26/12* (2014.01)
*B23K 28/00* (2006.01)
*B23K 37/047* (2006.01)
*A01N 1/02* (2006.01)
*B23K 26/361* (2014.01)

(52) U.S. Cl.
CPC .......... *A01N 1/0268* (2013.01); *B23K 26/361* (2015.10); *B23K 26/362* (2013.01); *B23K 28/00* (2013.01); *B23K 37/047* (2013.01); *B41M 5/24* (2013.01); *B41M 5/26* (2013.01); *B41M 5/262* (2013.01)

(56) References Cited

U.S. PATENT DOCUMENTS

| | | | |
|---|---|---|---|
| 9,358,091 B2 * | 6/2016 | Gilligan | A61D 19/024 |
| 9,358,541 B2 * | 6/2016 | Jimenez-Rios | B01L 9/06 |
| 10,071,582 B2 * | 9/2018 | Brehm | B41M 5/24 |
| 2008/0178988 A1 | 7/2008 | Ambartsoumian | |
| 2011/0126979 A1 | 6/2011 | Ambartsoumian | |
| 2011/0259892 A1 * | 10/2011 | Cognard | A01N 1/0268 220/560.11 |
| 2012/0089490 A1 | 4/2012 | Blaine | |
| 2014/0263115 A1 * | 9/2014 | Jimenez-Rios | B01L 9/06 211/74 |
| 2016/0074865 A1 | 3/2016 | Rao et al. | |
| 2017/0246897 A1 * | 8/2017 | Brehm | B41M 5/24 |

FOREIGN PATENT DOCUMENTS

| | | |
|---|---|---|
| WO | WO 91/02203 | 2/1991 |
| WO | WO 2009/029166 | 3/2009 |
| WO | WO 2014/063052 A1 | 4/2014 |
| WO | WO 2016/069984 | 5/2016 |

* cited by examiner

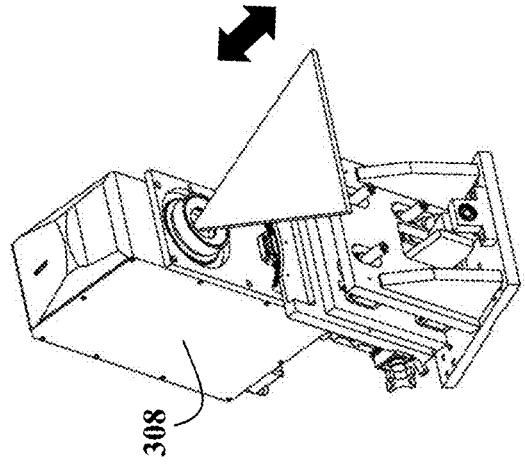
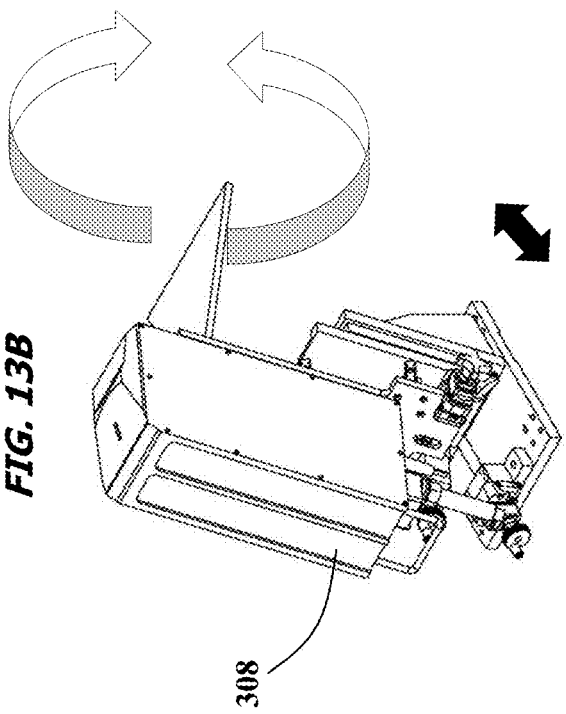
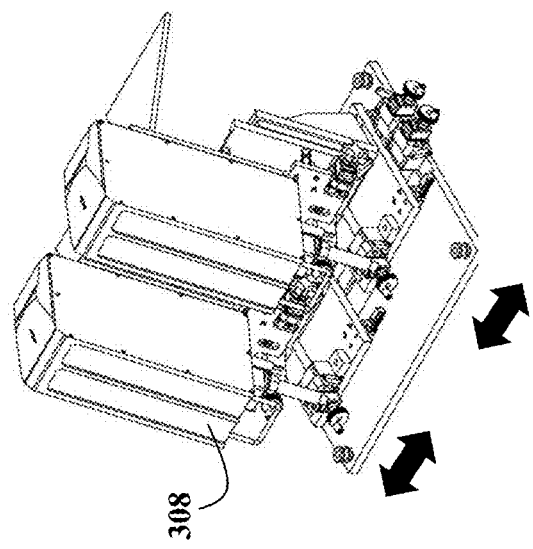
FIG. 13B
FIG. 13C
FIG. 13A

LASER ABLATION MACHINE FOR LABELING CRYOGENICALLY-FROZEN VIALS

CROSS-REFERENCE TO RELATED APPLICATIONS

This application claims priority to U.S. provisional application No. 62/330,071, filed 30 Apr. 2016, and incorporated herein by reference in its entirety. Reference is also made to International Application PCT/US15/58209, filed on 30 Oct. 2015, and herein incorporated by reference in its entirety.

INCORPORATION BY REFERENCE

All references cited below are herein incorporated by reference in their entireties.

FIELD OF THE INVENTION

This invention relates to an apparatus and method for imprinting a vial or ampoule, which is held at temperatures at around that of liquid nitrogen. More particularly, but not by way of limitation, this invention relates to a laser ablation printing system and method for printing onto a vial or ampoule that is at a temperature as low as the gaseous phase above liquid $N_2$ or the liquid phase of liquid $N_2$, at standard atmospheric pressure.

BACKGROUND OF THE INVENTION

Perishable biological materials, including immunological and vaccine compositions, must often be frozen to low temperatures, including that of liquid nitrogen, during storage and shipping. As a consequence, vials must be labeled prior to the freezing process, since, prior to the present application, there was no device for automatically labeling vials while maintaining the cryogenic temperatures. In situations where vials or ampoules contain veterinary and pharmaceutical medications (e.g. immunological compositions, including vaccines), certain information such as the type of medicine, dosage amount, manufacturer, expiration date, etc. must be clearly imprinted on each vial to remain in compliance with the regulations of the various regulatory agencies. Additionally, the number of vials or ampoules filled and the lot from which material originated are also very important data points to mark and track. Prior art labeling techniques include printing onto a label, and then placing the label onto the vials. More recent efforts include printing directly onto the vials (see U.S. Pat. No. 7,647,867, to Byron). In another example, US 20140048066 A1 (to Holitas Limited) describes the labeling of nebulizer ampoules by laser-marking or laser-engraving data on a film to produce a data film and affixing the film onto a nebulizer ampoule using a non-migratory adhesive. To date, applicants are aware of no method that allows frozen vials or ampoules to be labeled, while still preserving the integrity and efficacy of the biological material contained therein.

For multi-national pharmaceutical companies, where the same product requires different labeling (i.e. owing to different languages and different regulatory requirements), the ability to label a filled, frozen vial would be highly desirable. The benefits to the supply chain are obvious (e.g. faster lead time, less waste, increased flexibility, etc.). Unfortunately, raising the temperature of a frozen vial to the temperatures normally associated with label application and/or printing is well-known to unacceptably reduce the biological activity of the vial's contents. Thus, the application of heated labels, as disclosed in US 2008/0178988 A1 (to Ambarsoumian), would subject the sensitive biological material to unacceptable heating. Moreover, any efforts in using a laser or other means to directly mark the glass of the vial or ampoule would almost certainly subject the frozen biological material to unacceptable heat stress.

Accordingly, there remains a long-felt need to develop a method to label vials containing frozen medicaments, including vaccines, while retaining the required biological activity, including immunological activity. This disclosure provides a solution to this long-felt need.

SUMMARY OF THE INVENTION

Embodiments of the invention provide a machine for practicing a method of forming writings and graphics on a label, or other suitable substrate, held at cryogenic freezing temperatures, for example, at least as low as the gaseous phase above liquid nitrogen (i.e. about −196° C., or the boiling point of liquid nitrogen at standard atmospheric pressure). In accordance with one aspect of the invention, a method of forming a graphic on a label or substrate comprises applying a laser beam to a laser-active coating on a surface of an article to mark a writing or graphic in the laser-active coating.

The laser-active coating may comprise a polymer binder and a pigment, and optionally may contain additional ingredients. The coating formulation may contain at least a polymer binder having a glass transition temperature which provides a desired effect upon activation of the formulation by a laser beam, and a pigment having a heat resistance and present in a concentration which provide a desired effect upon activation of the formulation by the laser beam.

Suitable materials for "blank labels," which are ready to be ablated by the action of a laser beam, to reveal the desired writings or graphics, include, but are not limited to: plastics, acrylics, vinyls, polyethylene terephthalate (e.g., MYLAR®), polycarbonates (e.g. LEXAN®), or the like.

In a broad sense, this disclosure provides a cryogenic laser ablation machine, and methods of use thereof, for applying writings, graphics and/or markings to cryogenically frozen vials or ampoules. Throughout the process, the machine maintains the integrity, including the potency, efficacy, and/or safety, of the biological contents contained within the cryogenically-frozen vials.

In general, the lasers apply writings or graphics to the vials by ablating materials which had been placed on the vials prior to their having been cryogenically frozen. At a high level, the cryogenic laser ablation machine comprises the following elements (see e.g. FIGS. 1 and 2):

1. a housing, for containing and protecting the machine components (including their structural supports), and for protecting people from the various moving parts;

2. a first cryogenic freezer assembly, configured to connect to a cryostatic tunnel's proximal end, and containing an infeed assembly, into which a plurality of cryocanes, holding a plurality of cryogenically frozen vials ("cryovials" or "vials" or "ampoules"), is fed or loaded;

3. a cryostatic tunnel, configured to be attached to the first freezer assembly on the tunnel's proximal end, and configured to be attached to a second freezer assembly on the tunnel's distal end; and wherein the tunnel is configured to receive and be connected to laser and vision assemblies;

4. vision assemblies, configured to be mounted on the tunnel such that the vision assemblies may be used to determine whether the vials are properly oriented for labeling and whether the labeled vials have been properly labeled;

5. laser assemblies, configured to be mounted on the tunnel such that the laser assemblies may label or mark the vials by ablating "blank" labels, which had been previously applied to the vials;

6. a second freezer assembly, configured to be attached to the tunnel's distal end, and containing an outfeed assembly, out of which a plurality of cryocanes, holding a plurality of labeled vials, is unloaded, optionally into shipping or storage containers;

7. servo mechanisms, for singulating and orienting the cryocanes, and for moving the cryocanes from the entrance of the infeed assembly, into and through the cryostatic tunnel, and out of the tunnel and into the outfeed assembly;

8. optionally, a programmable user interface, which a user/operator may use to control some or all aspects of the machine's functioning; and 9. optionally, a main control system, which is capable of operating all aspects of the machine's function, and is in electronic communication with the programmable user interface when present.

At a high level, the method for labeling vials using the cryogenic laser ablation machine comprises the following steps:

1. applying a blank, laser-active label to a storage vial or ampoule;

2. depyrogenating/sterilizing the blank labeled vial or ampoule;

3. filling the vial or ampoule with product/material to be cryogenically stored/frozen;

4. placing the filled vials or ampoules into storage apparatus (e.g. ampoules may be placed into aluminum canes, which have been designed to secure the vials in a fixed position, and to present a large surface area for labeling, as disclosed herein);

5. freezing the vials or ampoules to temperatures as low as about that of liquid nitrogen at standard atmospheric pressure (or about −196° C.);

6. transferring the frozen vials or ampoules to long-term and/or permanent storage at a temperature as low as about −196° C.;

7. testing the frozen material for integrity, including potency or efficacy;

8. determining the dose presentation/product specifications based upon the activity test; wherein after satisfactory testing and release, the containers which meet required specifications will be retrieved from the long-term or permanent controlled storage area and placed into intermediate storage area, while maintaining the low temperature of about −196° C., to ensure the integrity of the biological material;

9. loading cryocanes containing the frozen vials into the infeed assembly of the laser ablation machine;

10. orienting the cryocanes for subsequent labeling;

11. moving the cryocanes beneath vision assemblies and laser assemblies;

12. determining whether the cryocanes and vials are properly oriented;

13. labeling the vials with lasers;

14. moving the cryocanes beneath quality checking vision assemblies;

14. determining whether the vials have been labeled correctly;

15. moving the cryocanes, which contain labeled vials, out of the tunnel and into the outfeed assembly; and 16. unloading the cryocanes, which contain the labeled vials.

Accordingly, it is an object of the invention to not encompass within the invention any previously known product, process of making the product, or method of using the product such that Applicant reserves the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (51 U.S.C. § 112, first paragraph) or the EPO (Article 83 of the EPC), such that Applicant reserves the right and hereby disclose a disclaimer of any previously described product, process of making the product, or method of using the product.

Other aspects of the invention, including apparatus, systems, methods, and the like which constitute part of the invention, will become more apparent upon reading the following detailed description of the exemplary embodiments and viewing the drawings. Like numbers refer to the same components throughout unless otherwise expressly stated.

BRIEF DESCRIPTION OF THE DRAWINGS

The following detailed description, given by way of example, but not intended to limit the invention solely to the specific embodiments described, may be best understood in conjunction with the accompanying drawings, in which:

FIG. 13A is a view of two laser assemblies 308, side-by-side. Servos move the assemblies along the path indicated by the bidirectional arrows;

FIG. 13B is a view of a single laser assembly 308. Servos move the assembly along the path indicated by the bidirectional arrows;

FIG. 13C is another view of a single laser assembly 308. Servos move the assemblies along the path indicated by the bidirectional arrows (i.e. toward and away from the centerline of the machine). The circular arrows indicate that the laser can also be rotated;

DETAILED DESCRIPTION

Figure 1:
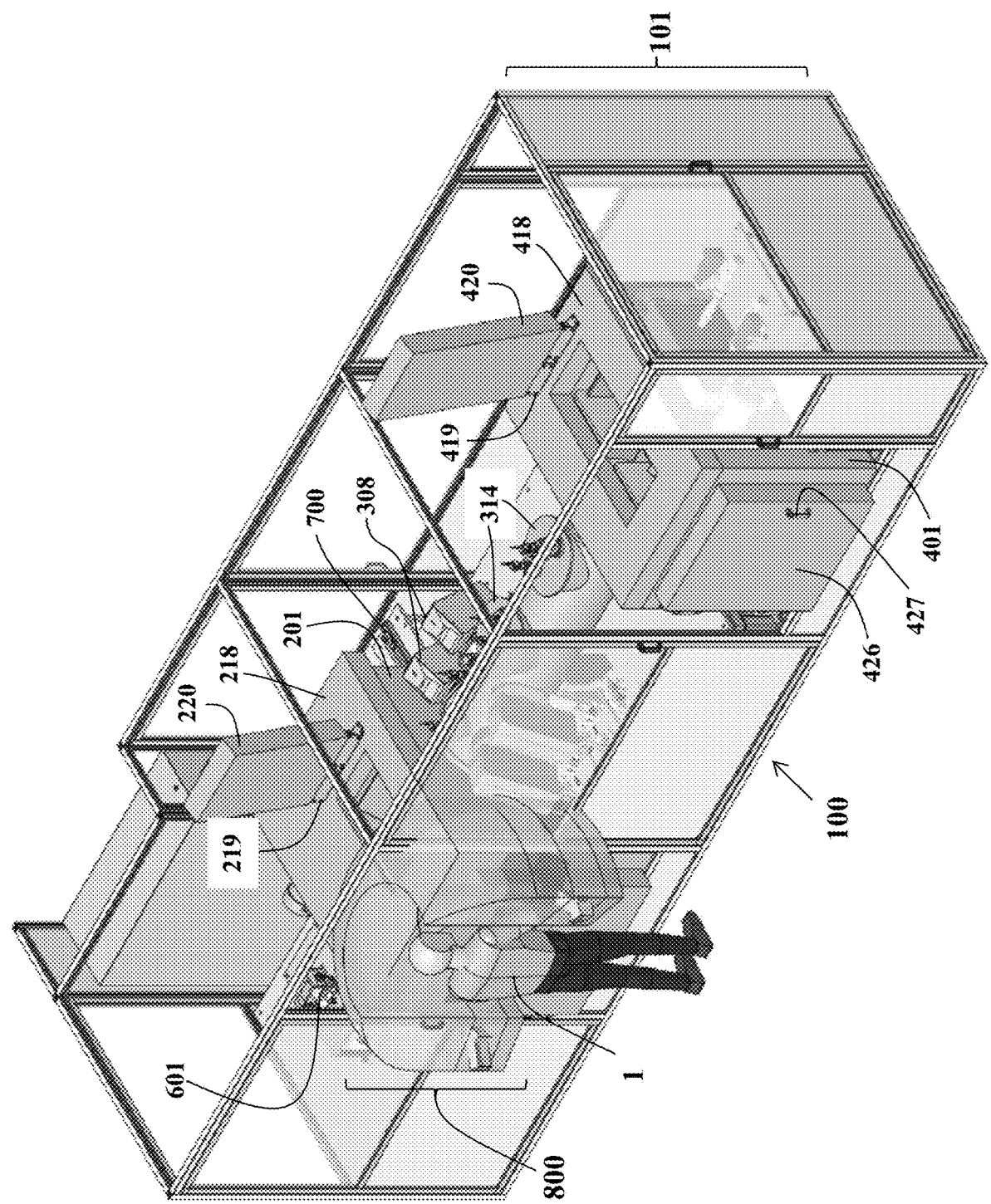
FIG. 1 is a perspective view of a cryogenic laser ablation machine 100 according to the disclosure. Prominent features include a machine housing 101; a rotatable shroud 800 for providing a user 1 access to the machine 100; a first cryogenic freezer assembly 200, containing an infeed assembly 230; a cryostatic tunnel 300, attached to vision assemblies 314 and laser assemblies 308; and, a second cryogenic freezer assembly 400, containing an outfeed assembly 430. In some embodiments, the machine comprises two (2) cryocane lanes, but the machine could also include only a single lane, three (3) lanes, or any other mechanically reasonable number of lanes.

FIGS. 1-10 show the overall configuration of a parallel in-line machine or apparatus for labeling or applying markings to cryogenically-frozen vials embodying the features of the present invention, which is denoted generally by reference numeral 100. The machine or apparatus 100 comprises a parallel in line system and includes a frame or frame structure, generally designated by reference numeral 101.

In some embodiments, the invention provides a laser ablation machine 100 for labeling cryogenically-frozen vials 40, which comprises:
- (a) an infeed assembly 230, contained within a first cryogenic freezer assembly 200, and configured to receive the cryogenic vials 40;
- (b) a cryostatic labeling tunnel 300, comprising an entrance opening at its proximal end and an exit opening at its distal end; wherein the tunnel 300 is configured to be equipped with at least one laser for labeling the vials 40;
- (c) an outfeed assembly 430, contained within a second cryogenic freezer assembly 400, and configured to dispense labeled vials 40;
- (d) a vial orienting means 639, for orienting the vials into a labeling position;
- (e) a vial pushing means 641, for pushing the vials sequentially from the infeed assembly 230 to and through the cryostatic tunnel 300, and from the tunnel 300 to the outfeed assembly 430;
- (f) at least one lane 350, beginning within the first freezer assembly 200, continuing through the tunnel 300, and ending within the second freezer assembly 400; wherein the at least one lane is configured to serve as a guide for the vials 40 as they are pushed through the machine 100;
- (g) optionally, a programmable user interface for enabling a user/operator to operate the machine in a completely or partially automated manner; and
- (h) optionally, a quality control means for determining whether the vials are positioned and labeled properly.

In some embodiments, the freezers may be cylindrical, rectangular, or any other mechanically suitable shape or configuration. The tunnel 300 may connect the first and second freezer assemblies via connecting ports and/or expansion joints. Suitable expansion joints include, but are not limited to, bellows-style joints 470. The tunnel 300 may also comprise one or more insulated viewports, composed of materials suitable for withstanding continual exposure to the cryogenic temperatures.

In some embodiments, the first cryogenic freezer assembly 300 comprises an opening through which a means for actuating the infeed assembly 230 may pass; and, the second cryogenic freezer assembly 400 comprises an opening through which a means for actuating the outfeed assembly 430 may pass. In general, the actuating means may be a rod or piston, or any other suitable means for operably connecting a servo-driven motor assembly to the infeed or outfeed assembly.

In some embodiments of the machine, the first cryogenic freezer assembly 200 comprises a first opening through which a means for actuating the infeed assembly 230 may pass, a second opening through which a singulating means 700 for singulating the vials 40 may pass, and a third opening configured to connect to the entrance or proximal end of the tunnel 300; and, wherein the second cryogenic freezer assembly 400 comprises a first opening through which a means for actuating the outfeed assembly may pass, and a second opening configured to connect to exit or distal end of the tunnel 300.

In some embodiments, the first cryogenic freezer assembly 200 comprises a freezer assembly lid 218, hingeably connected thereto via an assembly lid hinge means 219; and the second cryogenic freezer assembly 400 comprises a freezer assembly lid 418, hingeably connected thereto via an assembly lid hinge means 419. Each freezer assembly lid may comprise an access port through which vials 40 may be loaded or unloaded. Moreover, each access port may be selectably closable with an access port lid 220, 420, and each port lid may be hingeably connected to its respective freezer assembly lid 218, 418.

In some embodiments, the infeed assembly 230 may comprise a servo-driven infeed magazine wheel 235, configured to receive cryocanes 50 holding a plurality of vials 40 to be labeled. Prior to cryogenic freezing, a "blank label" is applied to the vials 40. As used herein, a "blank label" means a laser-sensitive material that may be marked or "datalased" by laser ablation. Vials loaded into the cryogenic laser ablation machine of the present disclosure are generally cryogenically-frozen and filled with a heat-labile biological material. In general, "heat-labile" means that the biological material will experience an unacceptable diminution of biological activity, including a loss of immunogenicity or a loss of efficacy, if the temperature is allowed to be increased above a certain safe level, or if the temperature is allowed to vary in a manner that may damage the biological material. In general, the machine may maintain a temperature of from about −150° C. to about −200° C. to prevent unacceptable losses in biological function of the frozen biological materials.

In some embodiments, the machine comprises a means for maintaining the vials 40 at a temperature that preserves the integrity of their contents from the time the vials 40 enter the machine to the time when labeled vials exit the machine. The means for maintaining the vials 40 at the integrity-preserving temperature may be a system that maintains a supply and level of liquid nitrogen ("LN$_2$") sufficient to maintain the required temperature. In an embodiment, the temperature maintaining means may be configured to receive an external supply of LN$_2$.

In some embodiments, the machine may comprise at least one temperature sensor, which is in operable communication with the programmable user interface, which is configured to allow a user/operator to select a maximum and minimum allowable operating temperature for the machine. In an embodiment, the machine comprises at least three temperature sensors, one contained within the first freezer assembly 200, a second sensor contained within the cryostatic tunnel goo, and a third sensor contained within the second freezer assembly 400. In some embodiments, each temperature sensor is operably connected to the programmable user interface, such that the user may select maximum and minimum allowable temperature variations within the freezers 200, 400 and the tunnel goo.

In other embodiments, the machine must maintain temperatures between about −150° C. and about −195° C. The machine may be configured to coexist with and be connected to existing or later-developed LN$_2$ systems. Each freezer system may have individual controllers for controlling the fluid level/temperature. When levels indicate, the controllers may open a cryogenic valve to allow LN$_2$ to fill the respective reservoir. In particular embodiments, each of the freezer systems may establish temperature zones for the material in station within the input magazine, in-process through laser ablation tunnel, and then in the outfeed magazine. Applicants envision that any manner of temperature regulation may be used in the practice of this invention.

In another aspect, the invention provides a method for labeling cryogenically-frozen vials 40 using the disclosed cryogenic laser ablation machine, comprising the steps of:

(a) providing a plurality of cryocanes 50, containing a plurality of blank-labeled vials 40, each containing heat-labile biological materials;
(b) loading the cryocanes 50 into the infeed assembly 230;
(c) singulating the cryocanes 50 by action of the singulator means 700;
(d) orienting the cryocanes 50 to present the vials' blank labels upward;
(e) moving the cryocanes 50 to a position beneath the laser assemblies 308; and
(f) labeling the vials with the laser assemblies 308, thereby labeling the cryogenically-frozen vials 40.

In some embodiments, the method further comprises the step of using a first or second camera 312, which are in operable connection with the programmable user interface, to determine whether the cryocanes 50 have been oriented such that the blank-labeled vials 40 are properly positioned beneath the laser assemblies 308.

In some embodiments, if the cryocanes are determined to be improperly positioned, a signal or alert is generated and communicated to the machine's user/operator and/or optionally stored within the programmable user interface.

In some embodiments, the method further comprises the step of using a first and/or second vision assembly 314, which is/are in operable communication with the programmable user interface, to determine whether the vials/ampoules have been properly labeled by the laser assemblies 308.

In several embodiments, if the vials 40 are determined to be improperly labeled, a signal containing details of this improper labeling is generated and communicated to the machine's user/operator and/or optionally stored within the programmable user interface.

In some embodiments, the method further comprises the step of using a first and/or second vision assembly 314, which is/are in operable communication with the programmable user interface, to determine whether the vials 40 have been properly labeled by the laser assemblies 308.

In other embodiments of the method, if the cryocanes 50 are determined to be improperly positioned and/or the vials 40 improperly labeled, a signal is generated to communicate this improper positioning and/or labeling information to either the user/operator, the programmable user interface, or both.

In still other embodiments, the method further comprises the step of increasing the speed of the labeling process if the cryocanes 50 have been determined to be properly oriented and the vials 40 have been determined to be properly labeled, marked or datalased. In some embodiments, the programmable user interface provides for automatic speed changes based upon information received from the vision assemblies 314. For example, the programmable interface may control the speed of all the servo mechanisms such that the machine begins a first speed, which is associated with an exceedingly high degree of labeling precision. As used herein, an "exceedingly high" degree of precision means that the machine properly labels >99.999% of the vials. Furthermore, as used herein, a "high" degree of precision means that >99.99% of the vials will be labeled properly; a "moderate" degree of precision means that >99.9% of the vials will be properly labeled; and a "low" degree of precision means that ≤99.9% of the vials will be properly labeled. Since the frozen biological materials, contained within the vials, are nearly always subject to regulatory agency oversight, the labeling precision is ideally at least high.

In some embodiments, the method further comprises the step of decreasing the speed of the labeling process, or stopping the labeling process, if the cryocanes 50 have been determined to be improperly positioned and/or improperly labeled.

In other embodiments, the method further comprises the step of accessing the interior of the cryostatic tunnel 300 to reposition an improperly positioned cryocane 50, or, to remove an improperly labeled vial 40.

In another aspect, the invention provides a cryocane 50, for use in the disclosed cryogenic laser ablation machine, and configured to receive and hold a plurality of vials 40. In a particular embodiment, the cyrocane securely holds at least five (5) vials throughout a complete labeling process. In more particular embodiment, the cryocane 50 is configured to securely hold the vials such that a significant portion of the vial's surface is available for laser ablation. This feature of presenting a large surface area for laser ablation significantly distinguishes the cryocanes 50 of the present application from prior cryocanes. Before the instant disclosure, most cryocanes secured the vials via integrated tabs that clasped the vials by their central portions. Such cryocanes are wholly incompatible with the disclosed laser ablation machine because insufficient blank label would be available to applying the required information to the vials. In contrast, the cryocanes 50 of the present disclosure are designed such that their integrated tabs clasp the vials 40 by their top and bottom portions, leaving a significantly larger surface area available for laser ablation labeling/marking/datalasing.

In general, now that the invention has been disclosed, the skilled person employing only routine work may produce a wide range of laser ablation machine configurations. For example, while 2 lanes 350 are depicted in the several drawings, any number of lanes 350 may be used in the practice of the invention. Moreover, any suitable configuration of $LN_2$ vacuum jacketed supply lines, gaseous nitrogen supply, electrical power supplies, and the like may be alternately configured and still remain within the scope to the present disclosure.

Furthermore, the placement of freezer assembly access doors may be varied (e.g. front, rear side, top, etc.) according to specific labeling requirements. Access doors or ports provide for machine assembly/disassembly and general maintenance. Likewise, the placement of the smaller top-mounted access doors/openings, which provide for load and unload access to the infeed and outfeed magazines, may vary according to specific requirements.

In some embodiments, upright freezers should be structurally designed to allow for $\geq$ about 1000 lbf internal loads at $\leq$ about 25 psi, (distributed load of mechanical mechanisms). The upright freezers should comprise internal mounting locations and pads with confirmed mounting hole patterns, dowel holes, and the like, for mounting machine components inside the freezers. The upright freezers should additional comprise external mounting locations and pads with confirmed mounting hole patterns, dowel holes, and the like, for mounting the freezers to the machine frame.

In some embodiments, the cryostatic tunnel goo may comprise end flange mounting locations (e.g. 371, 372) and viewport flange mounting locations (e.g. 321) with confirmed mounting hole patterns, dowel holes, and the like, for mounting to separate freezers and viewports.

In general, dangerous machine motions should be protected via interlock devices, service-only removable panels, and the like. In cases where freezer doors themselves serve as safety barriers, the machine may advantageously comprise and employ safety interlocks to prevent user/operator access to the machine while harmful motions or energy occurs. Where such precautions are not possible or otherwise contraindicated, actual guard doors with interlocks may advantageously be in place over the freezer access doors. Freezer manufacturers may provide mounting features for safety interlocks on all doors, and provide these desired interlocks. Such interlocks would terminate at the machine's main control system to establish overall safety topology.

In some embodiments, the machine comprises an evacuation means, which provides a means for evacuating $N_2$ or any other harmful substance. The machine may comprise a means for providing for automatic operation of the material handling operations.

In other embodiments, the machine comprises multiple temperature sensing devices, which coordinate with a programmable user interface and/or master controller to ensure that the desired set point temperatures around the product (e.g. vials containing heat-labile biological materials) are maintained at all times and locations.

In some advantageous embodiments, temperature sensors are present in at least the infeed and outfeed magazines, and at three locations within the tunnel.

In another embodiment, the machine has a means to provide and maintain a $N_2$ inert gas environment at a pressure of about ~0.1" w.c. ("w.c."=water column, in inches) within the freezers. Providing such a pressure serves to displace any oxygenated fresh air out of the freezer system and to limit condensation.

In some embodiments, the machine comprises a master control system, which may advantageously be configured to allow bidirectional handshaking and data transfer to a primary machine controls system. Examples include an Allen Bradley Compactlogix system with Ethernet IP communications. Other suitable control systems may be employed in the practice of this invention.

In some embodiments, the machine minimally contains the following instrumentation:
   (a) Each freezer comprises an individual internal control system to maintain the following
      a. minimum of three RTD or TC inputs;
      b. manual fill override; discrete or network I/O signals. These I/O signals to include:
      c. remote monitoring of Temperature conditions;
      d. fault outputs;
   (b) All above data must be able to be monitored by the primary or master controller (PLC); and
   (c) Controls for each freezer may be in individual enclosures, or combined into one.

In some embodiments, the freezers may be constructed of suitable materials (e.g. vacuum-jacketed cryogenic freezer wall), and of suitable sizes and configurations to conform to the dimensional constraints of the surrounding system. As an example, the tunnel 300 may be made of SCH10 pipe, or any other suitable type of pipe, for the majority of its components.

In other embodiments, the primary material for the machine may be 304 Stainless steel 2B finish, or better. Regardless of the choice of material, the materials must be corrosion-resistant or completely noncorrosive. In some embodiments, fasteners may comprises 18-8 Stainless Steel, 316 Stainless Steel, or better. Applicants envision that many routine material substitutions are possible, including substitution of materials that have not yet been developed.

In some embodiments, the machine comprises one or more viewports. In general, viewport materials may be selected to correspond with individual functions (e.g. when the laser wavelength is 1024 nm, the viewport must allow passage of 1024 nm light). In other embodiments, if the viewport is for visual inspection by a human's eye, it must be made of material that allows passage of visible light.

In an embodiment, laser viewports may comprise sapphire, quartz, fused silica or similar materials, to allow maximum transmission of the laser light.

In other embodiments, the machine comprises viewports for visible cameras and lighting. In advantageous embodiments, the viewports comprise at least two layers, with evacuated space maintained therebetween. Control and monitoring of this vacuum may be incorporated into the freezer control system, or into the main machine control system.

In some embodiments, the machine may comprise round- or square-shaped freezers. Moreover, the walls of the freezers may vary in thickness and means for providing insulation. In an embodiment, the freezers may be square or rectangular in shape with about 5" walls. In such an embodiment, the thickness provides the insulation, and vacuum jacketing may not be required. In other embodiments, the freezers are constructed as thinner-walled round shapes, with vacuum insulated walls.

In other embodiment, freezer designs advantageously limit the accumulation of liquid and frozen condensate on the outside of the units, or in any of the insulated areas.

In some embodiments, freezer designs do not have any exposed insulation (e.g. layers of Styrofoam on the lid, if used must be fully encased in covering plastic or other suitable material to prevent premature wear or flaking of insulation into the machine working area).

In advantageous embodiments of the laser ablation method, the entire method is carried out in cool, dry nitrogen gas, to eliminate the need to remove water vapor or frost. In such an embodiment, the disclosure provides a method for applying writings, graphics and/or other markings to frozen vials or ampoules, while maintaining the integrity of the biological material contained therein, comprising the following steps:
  a. providing a plurality of biological material-filled vials, which are held at about −150° C. to about −196° C., and to which blank laser-ablatable labels had previously been applied;
  b. loading the plurality of vials into the laser ablation machine, which is substantially filled with dry nitrogen gas to reduce or eliminate the presence of moisture inside the enclosure;
  c. conveying the vials beneath marking laser assemblies;
  d. applying laser light to the laser-ablatable labels;
  e. determining whether the vials have been marked to within required specifications, thereby applying writings, graphics and/or other markings to frozen vials, while maintaining the integrity of the biological material contained therein.

In some embodiments, the integrity of the biological material may be confirmed as having been maintained if the biological material is capable of eliciting an immune response in a target animal. The elicited response is statistically similar to the response elicited by the biological material contained within the plurality of vials prior to being subjected to the laser-marking method.

In an embodiment, the integrity of the biological material may be confirmed as having been maintained if the biological material is determined by ELISA, virus neutralization antibody (VNA) test, or any other suitable immunological measuring test, to be within the specifications required by the product specifications for the biological material.

In a particular embodiment, the vials, contained within cryocanes, may be pushed along one or more lanes, by servo-driven motor assemblies, which are operably connected to rods or other suitable pushing means. Alternatively, the cryocanes may be conveyed along a suitable conveyor means, such as a belt or a track. In an advantageous embodiment, two or more row of vials are pushed or conveyed beneath the marking lasers to increase the speed at which the vials may be marked.

In another embodiment, the method may further comprise the step of transferring the marked vials to a liquid nitrogen-containing shipping Dewar. Advantageously, the Dewar comprises a means for reversibly connecting to the marking enclosure, such that the marked vials may be transferred via a means for transferring the vials to the storage/shipping Dewar, without exposing the vials to the air outside of the enclosure.

In other embodiments, the invention provides a method for applying writings, graphics and/or other markings to vials held at a temperature from about −150° C. to about −196° C., while maintaining the integrity of the biological material contained therein, comprising the following steps:
  a. applying blank laser-ablatable labels to a plurality of cryogenic storage vials;
  b. depyrogenating/sterilizing the vials;
  c. filling the vials with biological material;
  d. placing the filled vials into a storage means;
  e. transferring the vials to a means for marking the vials with lasers;
  f. using a laser to apply writings, graphics and/or other markings to the vials, thereby applying writings, graphics and/or other markings to the frozen vials, while maintaining the integrity of the biological material contained within the vials.

In an embodiment, the method may further comprise the steps of:
  a. freezing the vials at a controlled rate of cooling, prior to placing the vials into the storage means;
  b. transferring the frozen vials to long-term and/or permanent storage at a temperature as low as the gaseous or liquid phase of $N_2$ (about −196° C.);
  c. testing the frozen material for activity;
  d. determining the dose presentation/product specifications based upon the activity test; wherein after satisfactory testing and release, the containers which meet required specifications will be retrieved from the long-term or permanent controlled storage area and placed into intermediate storage area to facilitate the steps recited in (j), all of which are conducted in the gaseous phase of $N_2$ to ensure product integrity;
  e. counting the containers to ensure adequate reconciliation for customer requests/orders;
  f. using a laser to apply writings, graphics and/or other markings to the ampoules or vials, based upon product specifications/information/approved label as defined by the testing, the customer specifications, and regulatory governance.

In advantageous embodiments, the applying of writings and markings step is carried out in a temperature-controlled enclosure containing dry nitrogen gas, which gas is held at temperatures below about −140° C. or below about −150° C.

In an embodiment, the method comprises the step of placing the marked vials into one or more cryogenic shipping vessel.

In some embodiments, the material in the vial is a vaccine, including a cell-associated live vaccine.

In advantageous embodiments, the vaccine loses less than about 0.2 log of titer during the labeling procedure. In an even more advantageous embodiment, the vaccine loses less than about 0.1 log of titer during the labeling procedure.

In an alternative embodiment, the method includes the following steps:
1. applying a blank, laser-active label to a storage vial or ampoule;
2. depyrogenating/sterilizing the blank labeled vial or ampoule;
3. filling the vial or ampoule with product/material to be cryogenically stored/frozen;
4. placing the filled vials or ampoules into storage apparatus (e.g. ampoules placed into aluminum canes);
5. freezing the vials or ampoules to temperatures as low as about that of liquid nitrogen at standard atmospheric pressure (i.e. about −196° C.);
6. transferring the frozen vials or ampoules to long-term and/or permanent storage at a temperature as low as about −196° C.;
7. testing the frozen material for integrity, including potency or efficacy;
8. determining the dose presentation/product specifications based upon the activity test; wherein after satisfactory testing and release, the containers which meet required specifications will be retrieved from the long-term or permanent controlled storage area and placed into intermediate storage area, while maintaining the low temperature of about −196° C., to ensure the integrity of the biological material;
9. using the disclosed laser ablation machine to apply writings, graphics and/or markings to the blank labeled ampoules or vials based upon product specifications/ information/approved label as defined by the testing, the customer specifications, and regulatory governance; thereby applying the writings, graphics and/or markings to the cryogenically frozen ampoules or vials.

In yet another embodiment, the entire method may be carried out at less than about −140° C., −150° C., −160° C., −170° C., −180° C., −190° C., or less than about 200° C.

Use of such a laser ablation technique allows for additional label layers to be included as needed, for example, to prevent thermal transfer during the frost removal or laser ablation steps. It is essential that the integrity/efficacy/ potency of the cryogenically frozen biological material is maintained during the entire process.

The nature of the label material is not particularly limited. The label substrate must be able to adhere to the ampoules or vials at about room temperature and stand up to the subsequent sterilization and cryogenic freezing processes. Representative classes and examples of label materials that may be utilized include, but are not necessarily limited to, plastics, acrylics, vinyls, polyethylene terephthalate (e.g., MYLAR®), polycarbonates (e.g. LEXAN®) or the like.

In an embodiment, the product testing includes potency testing, which may include the determination of titer or plaque forming units (PFU's).

In an embodiment, labels may comprise multiple layers. The multiple layers may comprise a primary (interior) layer which may be, for example, dark or black, or, light or white. If the interior layer is light or white in color, the marking may be dark or black. Conversely, if the interior color is dark or black, the marking color may be light or white.

In an embodiment, the secondary (outer) layer may be colored coded based upon marketing preference. Variable coloring allows for visual differentiation of container contents or material specifications.

Additional layers may be added to allow for further differentiation of material/ containers. In an embodiment, the primary or interior layer(s) is a polyester face stock. The secondary/additional layer(s) may be a colored polyester face stock.

In an embodiment, the laser ablation method provides color-coding for different types of biological products. For example, all Marek's Disease vaccines could have an orange label with black lettering. All combinations of background and foreground colors are contemplated, for example, but not limited to white lettering on black background, white lettering on blue background, white lettering on purple background, and so on.

In another embodiment, "datalase" (DataLase Inc.) labels may be used. This technology uses a combination of color change chemistry and low power laser light. In such an embodiment, all of the other steps would be the same (e.g. blowing away the light-blocking cloud and using a laser to remove the frost layer from the surface of the label). The only step that would change is that "datalasing" would be used in place of laser ablation.

In some embodiments, the laser may be selected from one of ID Technology's "Macsa" range of lasers, including, but not limited to, the K1010 plus laser. In another embodiment, an Ultra High Speed (UHS) laser may be used. In yet another embodiment, an extremely powerful 80 w laser may be used. Now that applicants have made the instant disclosure, those skilled in the art may employ any number of suitable lasers to practice the invention. $CO_2$ and YAG pumped diode lasers are among the many possible choices.

In a particular embodiment, the laser may have the following characteristics:
  Ability to print two (2) lines of text at 16,000 units per minute;
  A digital circuit board driving a fast mirror tracking system;
  Consistent, high-quality, permanent marking;
  Ability to mark on labels, cardboard, PET, glass, coating and wood;
  Ability to operate with a handheld terminal, touch screen or PC;
  Available in 30 and 60 watt power.

For example, IDT Laser Systems "SHS" Laser Coders utilize digital circuit boards to control its mirrors, freeing the laser to mark at super high speeds. Applying laser energy quickly and efficiently may reduce the amount of heat to which the frozen ampoules must be subjected during the frost removal and laser marking steps.

In some embodiments, multiple lasers may be used. For example, a more powerful laser may remove the frost, and a less powerful laser may ablate the outer label to produce the marking. Alternatively, the same laser may serve both functions of frost removal and label layer ablation.

In some embodiments of the laser ablation machine, an operator loads aluminum canes housing ampoules into the machine, with the cane heads commonly oriented. The canes are typically held within "cages", which can be transported in cryogenic carts, so the loading step may involve taking a cage out of a cryogenic cart and "pouring" the canes into the infeed hopper. After receiving the canes into the hopper, the machine singulates the canes (i.e. separates the bulk canes into single canes), radially orient them, and then indexes the canes through the machine for presentation to the laser markers. After marking, the canes may be inspected for part presence, basic quality and print presence. Passing the marking section of the machine, the canes are next presented to a pass/fail outfeed assembly. From this section, the marked and inspected canes can be unloaded by the operator for downstream processing.

An important advantage of the presently disclosed laser marker machine is that it maintains the sensitive frozen biologicals at a safe temperature throughout the loading, marking and unloading processes. By "safe temperature" it is meant that a given biologic will retain all or substantially all of its desired biological activity throughout the marking process. As such, all mechanical functions of the laser marker are ideally maintained at ≤−150° C. When ampoules are positioned to be marked, they may be in an open air, cryogenically cooled tunnel for between about 4 to about 12 seconds; or between about 6 to about 10 seconds; or about 8 seconds. This amount of time allows the lasers to mark the ampoules in the absence of complex viewports (i.e. in some embodiments, cameras alone may be sufficient).

In some embodiments, the upright $LN_2$ cryogenic freezers comprise the following features and/or characteristics:

(a) capable of providing low temperatures between about −120° C. and about −150° C. during their operation, the selected set point has to be maintained with a maximum variation of 10° C. below or above the set point;

(b) SS 304 freezer body, inclusive of internal reinforcements;

(c) freezer front door with locking mechanism;

(d) freezer top doors with smaller size access doors to allow for load/unload access to infeed and outfeed magazines; the magazines may be star wheels (e) pneumatic cylinders for opening/closing of large top doors;

(f) pneumatic cylinders for opening/closing of small access doors;

(g) outside the freezer enclosure, a complete supply train including:
  ½" SS union coupling for connection to $LN_2$ supply line;
  ½" NPT SS Rego safety relief valve;
  ¼" NPT, SS pressure gauge;
  ½" SS cryogenic block valve;
  ⅛" NPT, SS pressure gauge;
  ½", SS cryogenic proportional control valve;
  ⅛" SS pressure gauge (h) the freezer bodies and doors may be insulated by means of three (3) layers of the super insulation material cryogel and PU (CFK free) injected under pressure. Other suitable insulation means may be employed in the practice of the invention disclosed herein;

(i) inside the freezer bodies, the following may be provided:
  a fully stainless steel (SS) cold gases radial recirculation fan of which the variable speed drive motor with extended shaft mounted on the cabinet outside sidewall;
  a $LN_2$-injection spray nozzle assembly mounted at the outlet opening of the recirculation fan;
  a first temperature sensor (e.g. a Pt100 or other comparable sensor), to allow the machine control mechanisms to regulate the temperature inside the cabinet;
  a second temperature sensor, installed in close proximity to the bottom floor of the freezer, to indicate when the temperature at the coldest point of the freezer has risen above 0° C. (allows the processor to instruct the initiation of the clean in place (CIP) process inside of the freezer;
  a supply of CIP fluid to a maximum of about two (2) CIP spray balls installed in each freezer space;
  a CIP drain valve with positioner at the bottom of each freezer;
  sloped floor to allow for drainage of condensed water and/or CIP fluids;

(j) air heater built into the housing of the air recirculation fan of the cabinet. The heating element may be used to accelerate the defrosting and the drying of the cabinets after CIP;

(k) insulated SS top door, with dimensions of about 15 to about 25 inches by about 25 to about 35 inches; or, about 20 inches by about 30 inches. The top door may be opened and closed manually, but in particular embodiments, a pneumatic cylinder is used to open and close the door. A proximity switch is optionally operably connected to the door;

(l) insulated SS side door, optionally operably connected to a proximity switch;

(m) SS front door with solid SS hinges and a double cryogenic seal. The front door may have an interlock system (safety lock). In some embodiments, an electromagnetic door locking system may allow the door to be locked throughout the freezing cycle. A programmable logic controller (PLC) may provide for fully automated control of the locking mechanisms(s). For example, once the door is locked by the PLC, an operator of the disclosed laser ablation machine may be prevented from opening the door during the freezing cycle.

In some embodiments, each freezer cabinet may have an exhaust port(s) having a diameter of about 4" to about 8", or about 6" (150 mm), situated on top of the chamber, and configured to connect to exhaust piping.

In some embodiments, the machine comprises components for $LN_2$ refrigeration, ventilation, temperature sensors, exhaust piping, ports and fittings, connecting boxes, a main power supply/power supply panel and a programmable logic controller (PLC). The machine may comprise a suitable user interface for programming the PLC.

In some embodiments, the control system may be a Rockwell Automation based system. The controls may be based around a central PLC-based architecture, which may minimize configuration programs required to maintain the equipment. In particular embodiments, Ethernet networking is used to accommodate communication among the various components. Other forms of communication are envisioned, and other controllers may be present in the overall machine.

In some embodiments, the central laser ablation machine controller is a Rockwell Automation COMPACTLOGIX™ PLC, which communicates with other machine equipment and/or components via an internal Ethernet network. The network switches are ideally managed and sized appropriately.

In some embodiments, multiple servo-driven axes may be controlled via Rockwell's KINEXTIX® family of servo drives. Moreover, the laser systems may communicate to the PLC via Ethernet, allowing for control and data to be transferred to the lasers. The vision systems will also communicate to the PLC via Ethernet, allowing for control and proper vision inspection criteria to be transferred to the cameras.

In some embodiments, programming may be implemented in Ladder Logic, where this pertains to conventional machine control functions. Data searches and calculations may be facilitated using structured text programming.

In some embodiments, alarms may be latching and require acknowledgement or reset from a human machine interface (HMI).

In some embodiments, HMI programming for the machine includes, but is not limited to: (a) a machine overview screen, which may show machine status and production counts; (b) a production selection screen, which allows an Operator to enter, for example, lot numbers, product codes, quantities and laser data); (c) a machine settings screen, optionally password protected, for modifying servo positions, speeds, critical timers, and linear cylinder positions; (d) a diagnostics screen, which may display the servo and electric cylinder positions; (e) a maintenance screen, optionally password protected, where actuators can be manually actuated for maintenance; (e) a current alarms screen, which may display active alarms; (f) an alarm history screen.

In some embodiments, freezers may comprise an internal control system comprising: (a) a plurality of temperature sensors to interface with the controller allow for the maintenance of consistent temperatures throughout the machine; (b) a manual fill override; (c) I/O signals, including temperature monitoring; fault outputs; and wherein (a), (b) and (c) may be monitored by the primary controller (PLC).

In some embodiments, a central exhaust may operably connected to the laser ablation portion of the machine. In such embodiments, the exhaust is useful for removing unwanted gases, vapors and particulates. A temperature sensor may be affixed to the machine to monitor the temperature of the exhaust.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicates otherwise. Finally, "about" has the ordinary meaning of "plus or minus 10%."

The invention is further illustrated by the following non-limiting examples.

EXAMPLES

Detailed Description of the Primary Embodiment.

Figure 2:
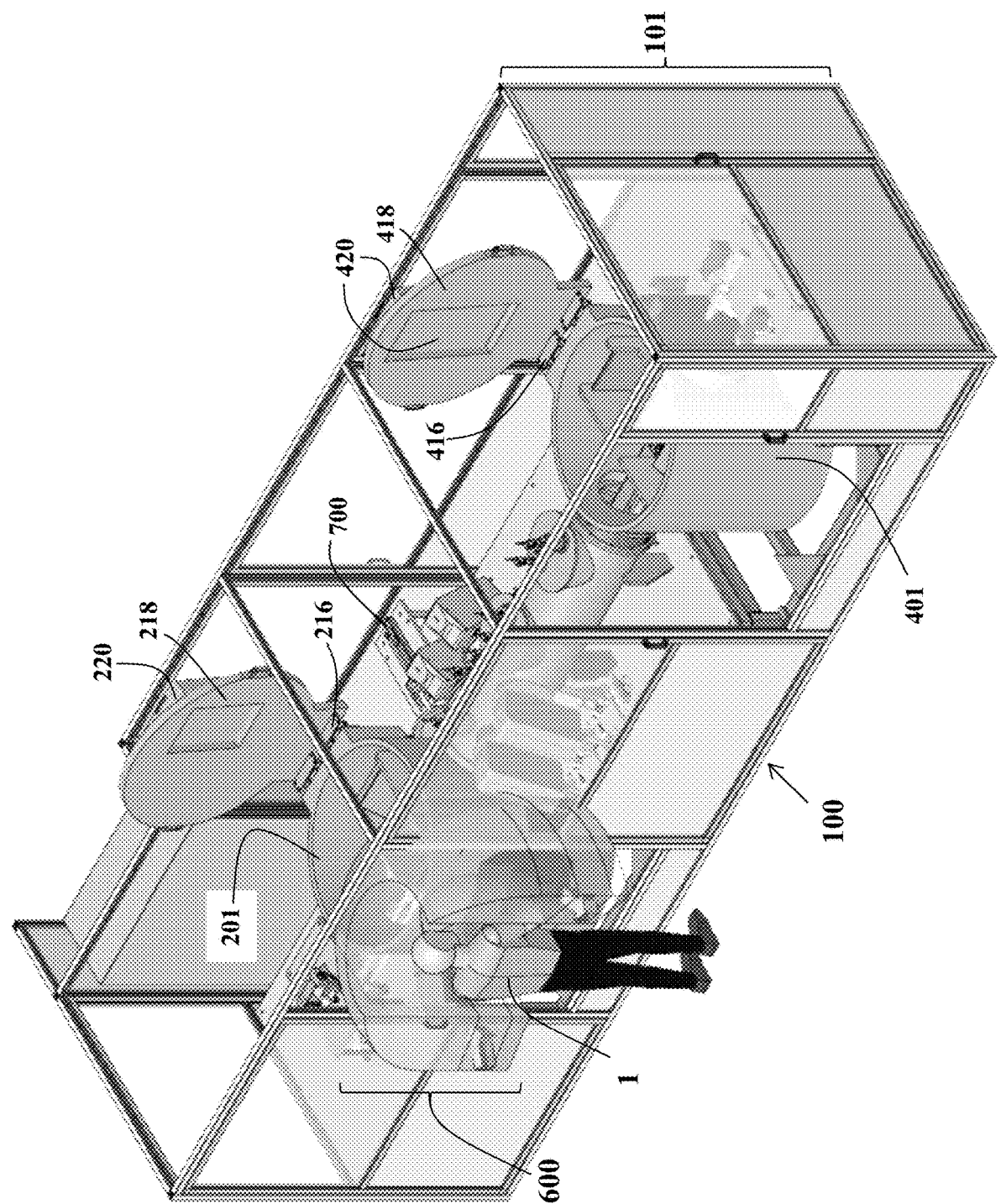
FIG. 2 is a perspective view of another embodiment of the cryogenic laser ablation machine 100. In this embodiment, the first and second freezer assemblies are cylindrical rather than rectangular.
Figure 3:
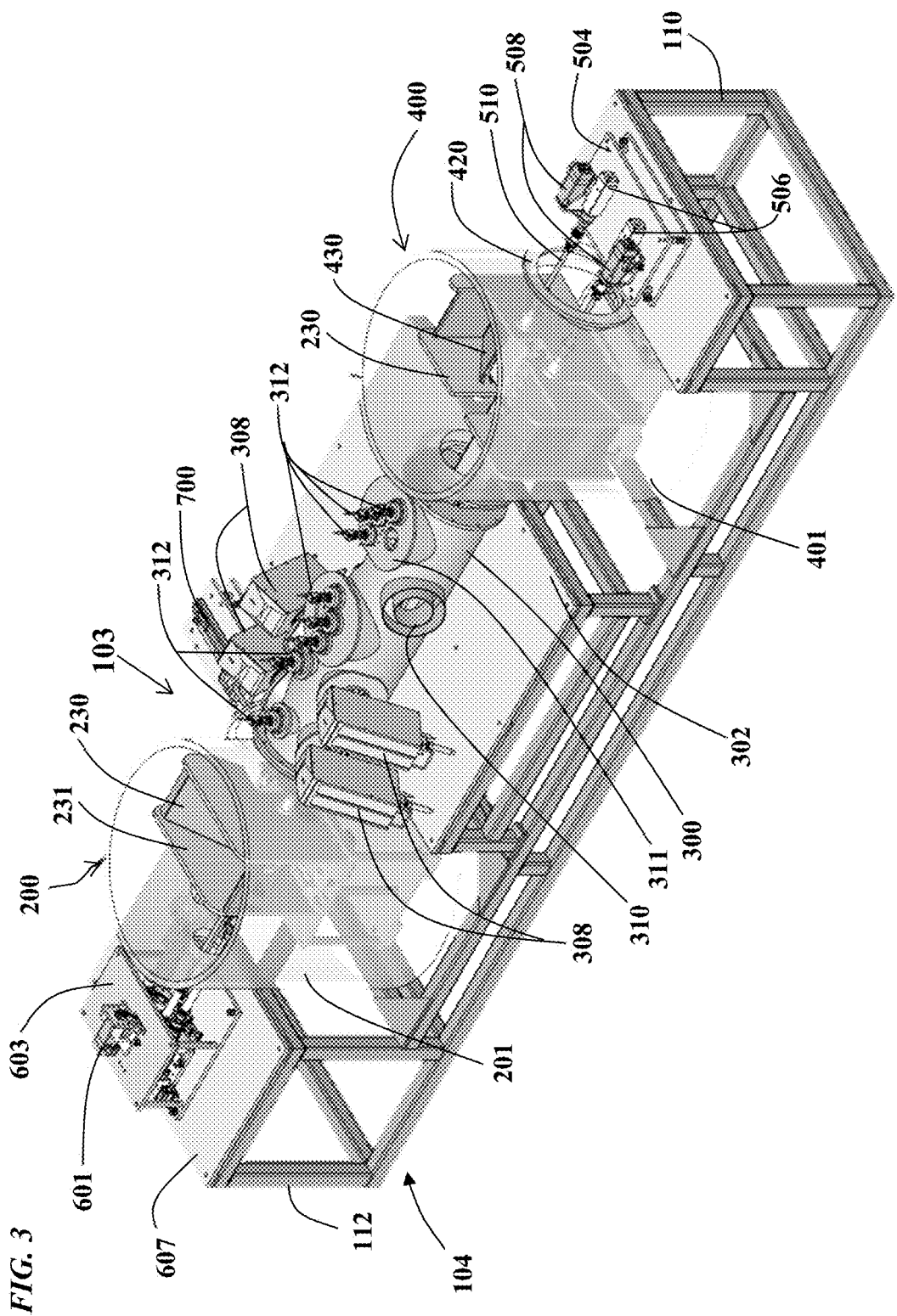
FIG. 3 is a view of the machine with its housing 101 removed, and showing: the infeed servo 600, operably connected to the infeed assembly 230, contained within the first freezer assembly 200, connected to the tunnel 300, connected to the second freezer assembly 400, which contains the outfeed assembly 430, which is operably connected to the outfeed servo assembly 500. The machine frame 104 serves as a foundation for the servo mechanisms, freezer assemblies and cryostatic tunnel 300.
Figure 4:
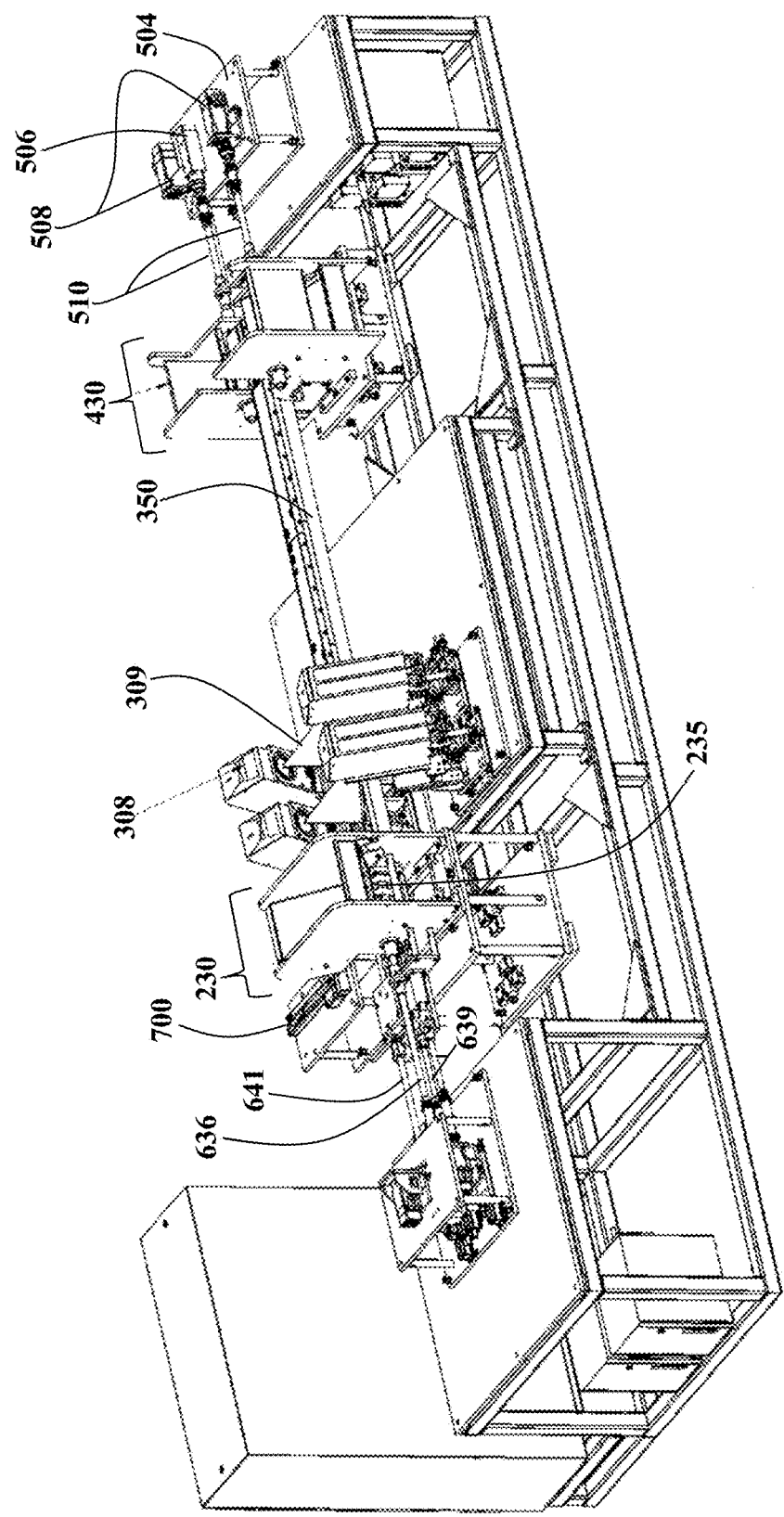
FIG. 4 is a view of the machine with the housing 101, the first freezer 200, the tunnel 300 and the second freezer 400 removed, to allow visualization of the internal components. As shown, cryocane-pushing rod(s) 639 operably connects the infeed servo assembly 600 to the infeed assembly 230, by communicating the lateral motion of the servo-driven motors to move the cryocanes through the machine from infeed assembly 230 to outfeed assembly 430. With the tunnel 300 removed, cryocane lanes 350 are readily visualized.

In an embodiment, the cryogenic laser ablation machine is substantially as depicted in FIGS. 1-10. As shown in FIGS. 1 and 2, the machine 100 comprises a machine housing 101; a rotatable shroud 800 for providing a user 1 access to the machine 100; a first cryogenic freezer assembly 200, containing an infeed assembly 230; a cryostatic tunnel 300, attached to vision assemblies 314 and laser assemblies 308; and, a second cryogenic freezer assembly 400, containing an outfeed assembly 430. As shown in FIG. 4, the machine comprises two (2) cryocane lanes 350, for guiding the cryocanes 50 throughout the machine, from the infeed assembly 230 to the outfeed assembly 430. The lanes span the length of the machine, from infeed assembly 230 to outfeed assembly 430, and are contained within the combination of the first freezer assembly 200, the tunnel 300 and the second freezer assembly 400.

As shown in FIG. 3, the machine comprises an infeed servo assembly 600, which is operably connected to the infeed assembly 230, which is contained within the first freezer assembly 200. As such, the first freezer tank 201 contains an opening through which the infeed assembly servo mechanism rods 636, 639 and 641 passes (see FIG. 4).

The first freezer assembly is sealably connected via a flange to the cryostatic tunnel 300, which is sealably connected via a flange and bellows extension joint 470 (see FIG. 6) to the second freezer assembly 400, which contains the outfeed assembly 430. The outfeed assembly 430 is operably connected to the outfeed servo assembly 500 via rods 510, which operably connect to the outfeed assembly through an opening in the second freezer assembly tank 401. As shown in the Figures, the machine frame 104 serves as a foundation for the servo mechanisms, freezer assemblies and cryostatic tunnel 300.

Figure 7:
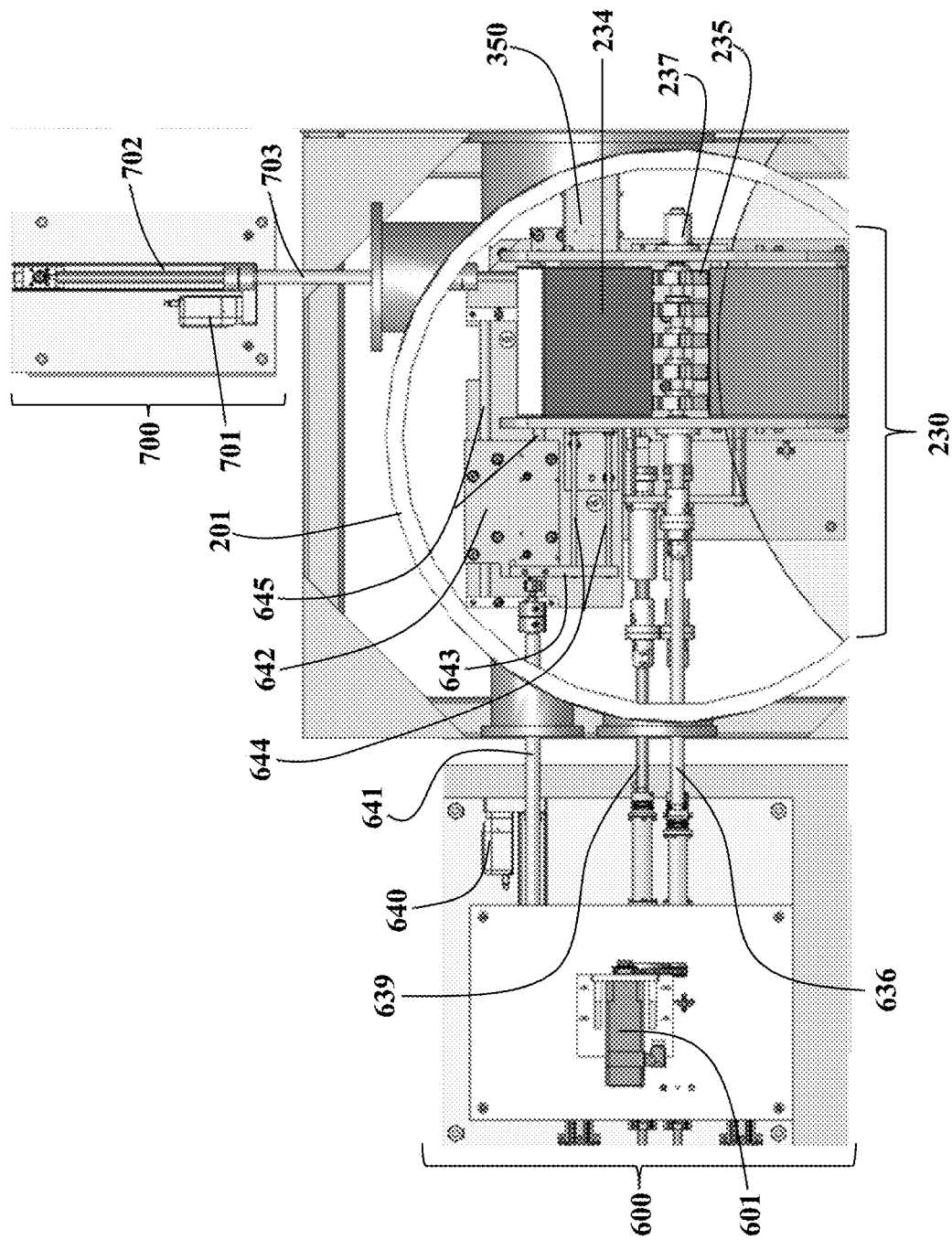
FIG. 7 is a top view of the machine, focused on the external infeed servo assembly 600, the infeed assembly 230 and the cryocane singulator assembly 700.
Figure 8:
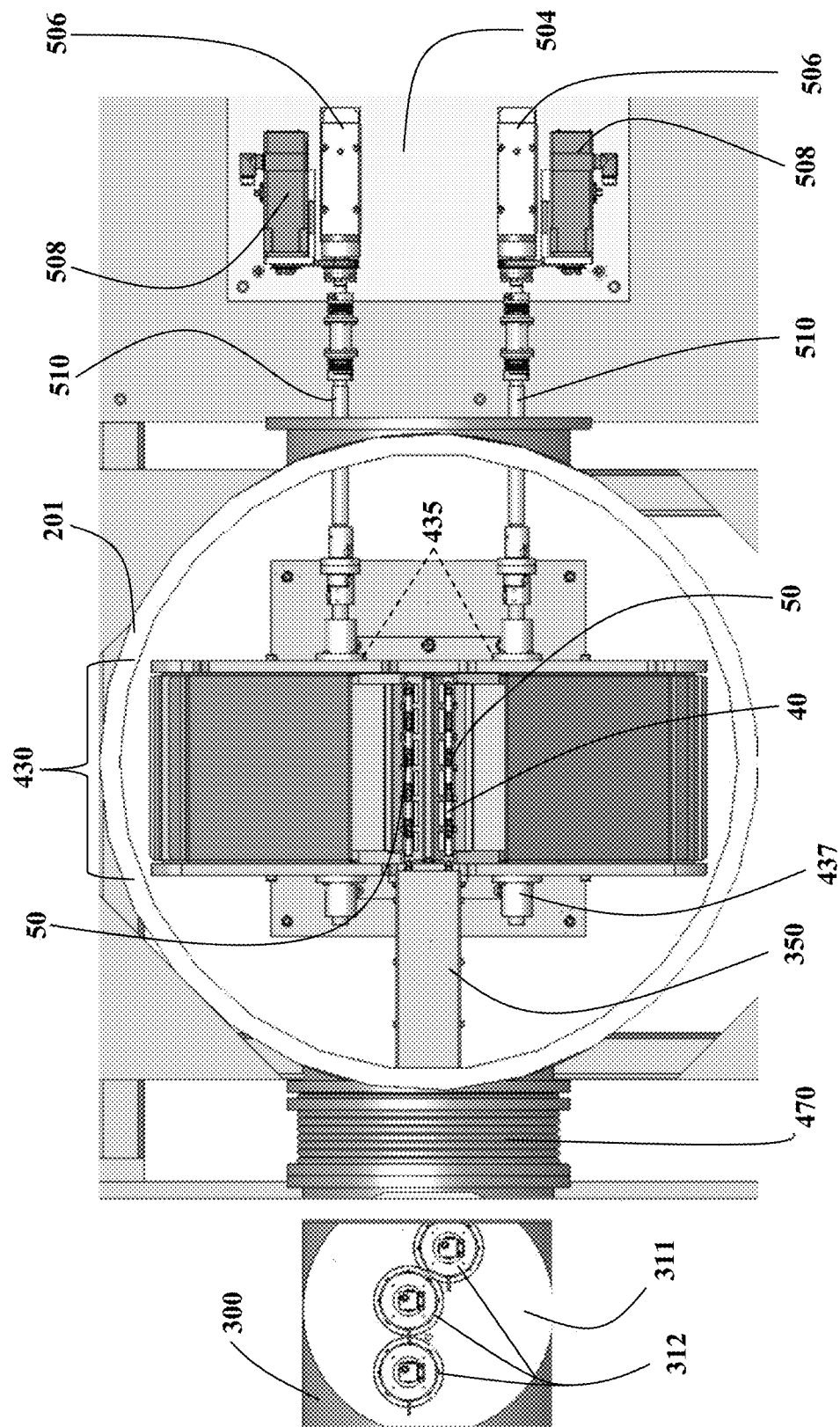
FIG. 8 is a top view of the machine, focused on the distal end of the cryostatic tunnel 300, the downstream vision assembly 314, the bellows connector 470, the second freezer assembly tank 200, the outfeed assembly 430 and the external outfeed servo assembly 600.
Figure 9:
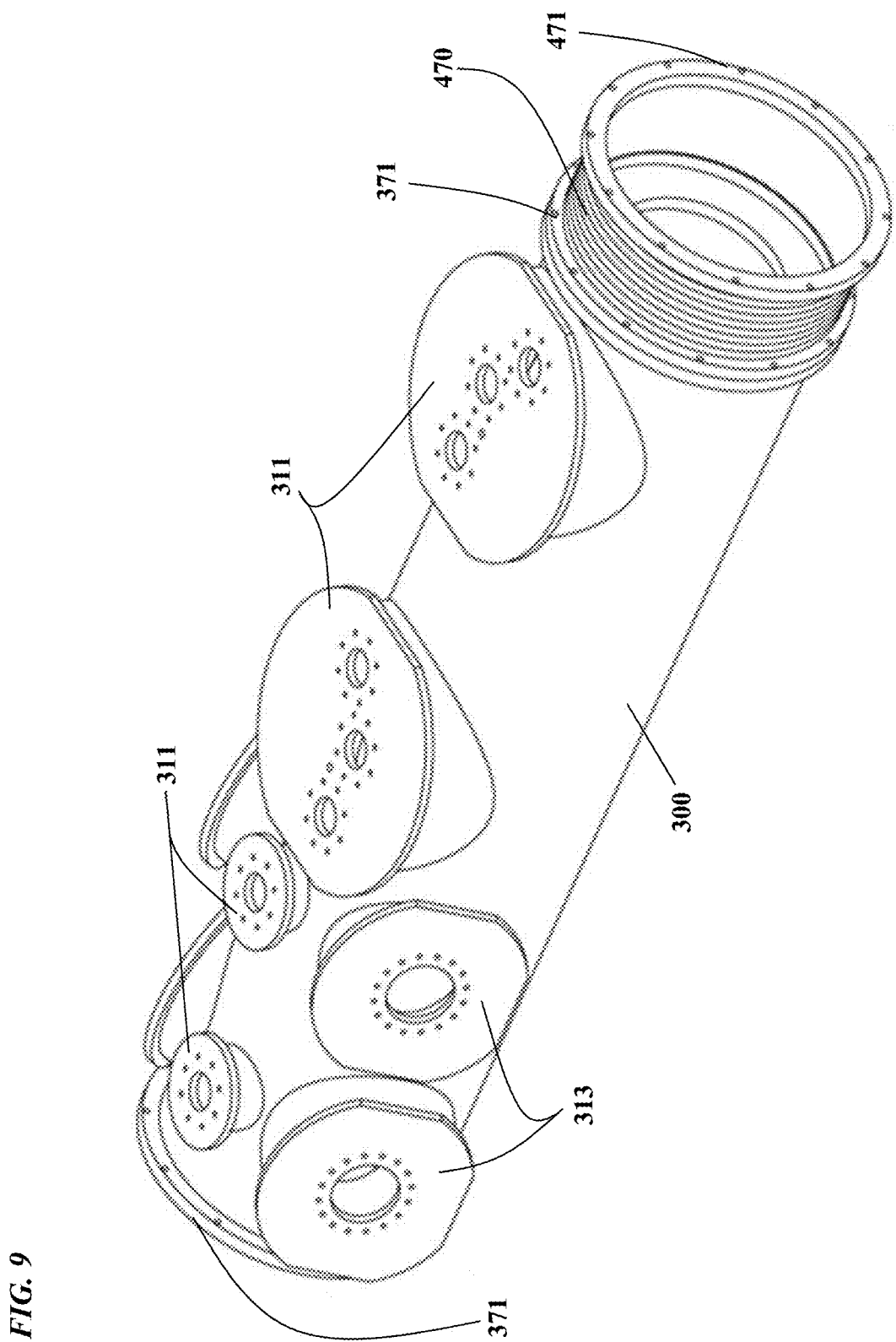
FIG. 9 is a perspective view of a cryogenic tunnel 300. Laser assemblies 308 may be affixed to the tunnel via laser assembly flanges 313; and camera/vision assemblies may be affixed to the tunnel via camera/vision assembly flanges 311. A bellows connector 470, comprising a bellows flange 471, allows for contraction and expansion between the tunnel 300 and the second freezer assembly 400.
Figure 10A:
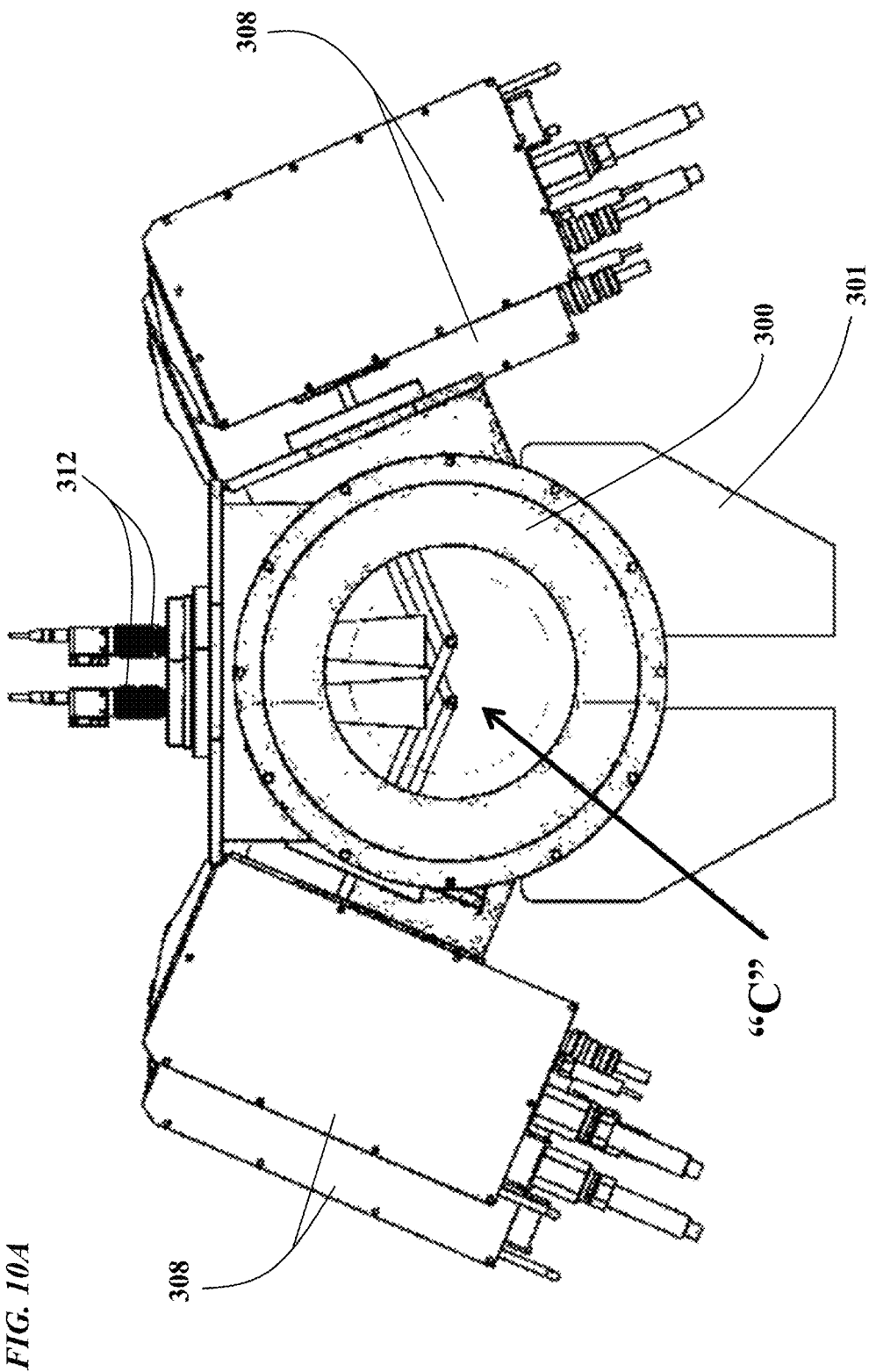
FIG. 10A is a cross-section of the tunnel 300 where the laser assemblies 312 are mounted thereto.
Figure 10B:
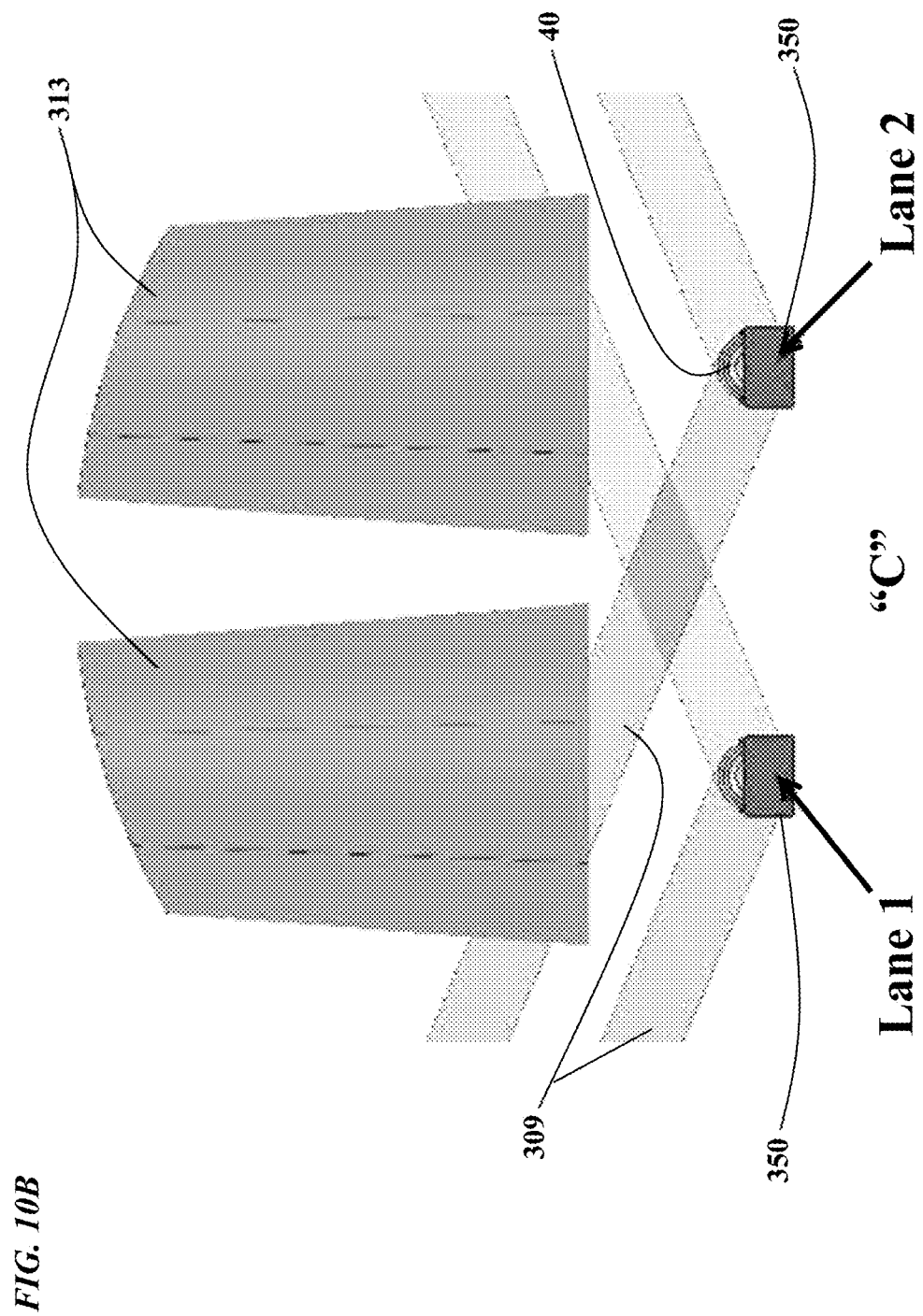
FIG. 10B is an enlarged section of FIG. 10A detail "C" and shows laser light 309 intersecting with the vials 40 carried by lanes 1 and 2 (i.e. machine feature 350). Shown also is the field of view 313 of the cameras 312.

As shown in FIG. 4, a main index rod 641 operably connects the infeed servo assembly 600 to the infeed assembly 230, by communicating the lateral motion of the servo-driven motors to move the cryocanes through the machine from infeed assembly 230 to outfeed assembly 430. As shown in FIG. 7, the movement of the index rod 641 is coupled to the movement of a pushing plate 643, a cryocane pushing rod 644 and a sliding plate 645, which is configured to slide along rails 645. Configured thusly, when the main index rod 641 moves to the right, the cryocanes are moved sequentially along the lanes 350 from the infeed assembly 230, into the tunnel 300, underneath the laser assemblies 308 and cameras 312, underneath quality control vision assemblies 314, out of the tunnel 300 through the bellows joint 470 and into the outfeed assembly 430.

Figure 5:
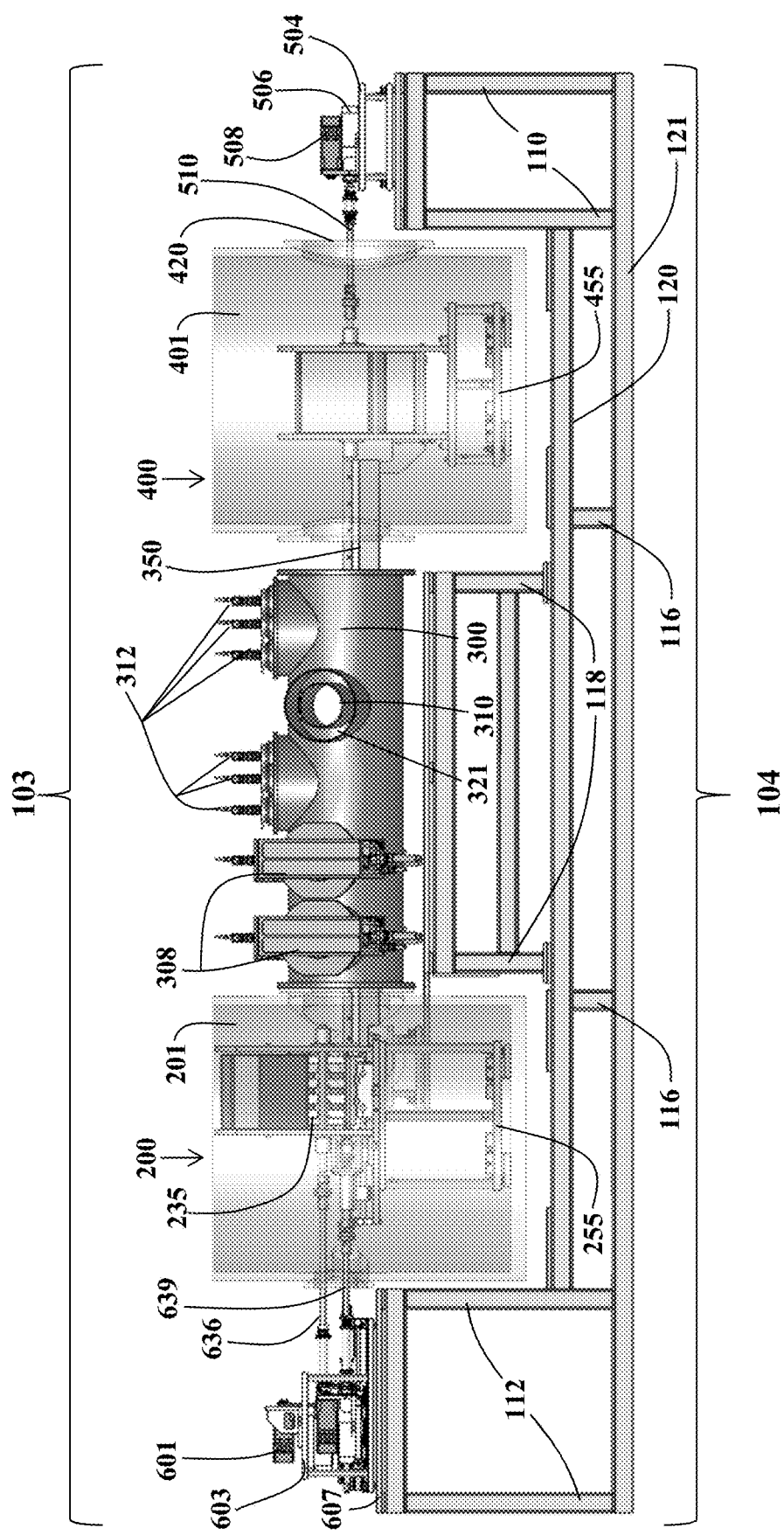
FIG. 5 is a side view of a laser ablation machine. As shown, magazine wheel rod 636 operably connects the infeed servo assembly 600 to the infeed assembly 230, by communicating rotational motion of the servo-driven motors to the infeed magazine wheel 235.
Figure 6:
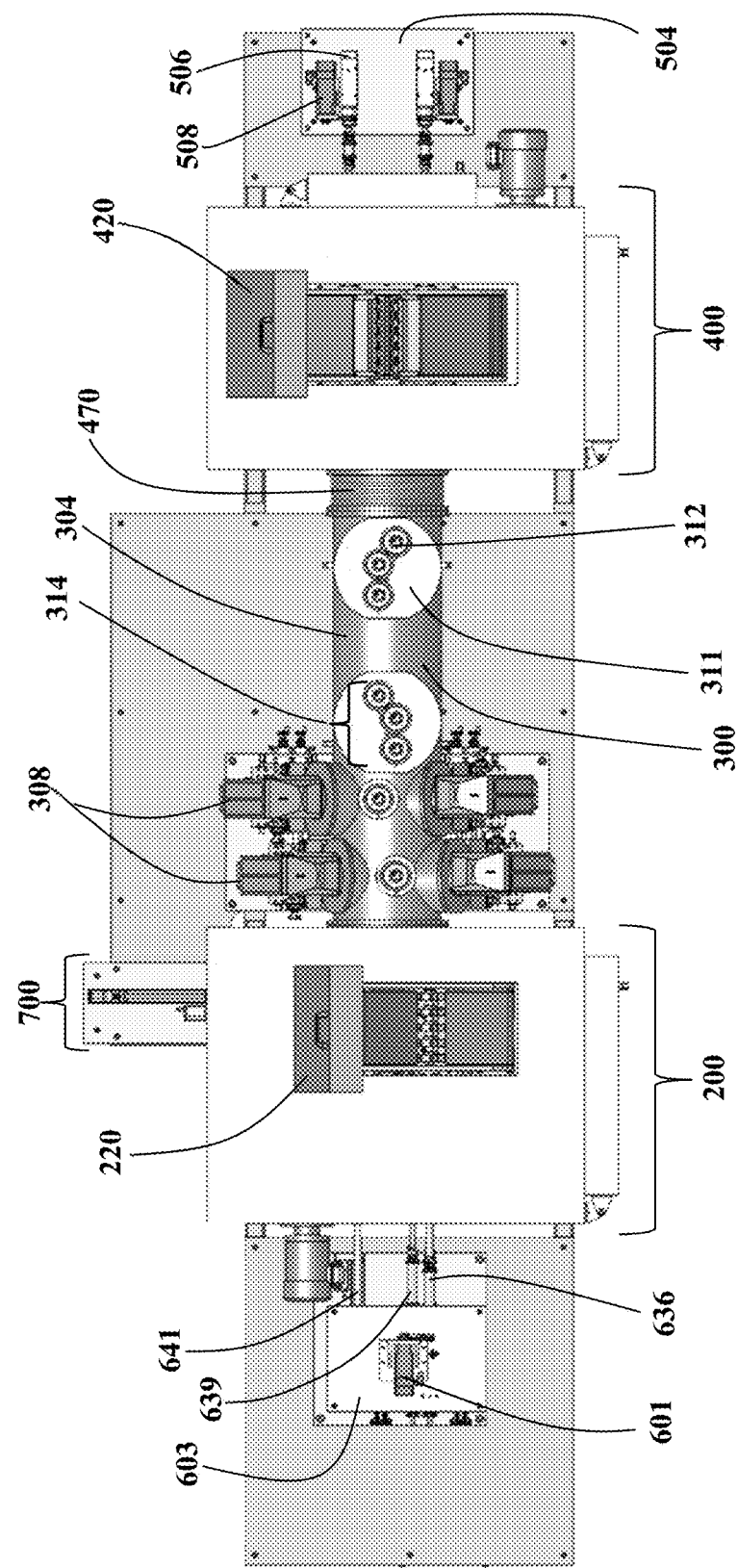
FIG. 6 is a top view of a laser ablation machine 100. As shown from this view, the infeed servo mechanism assembly 600 is operably connected to the infeed assembly 230 via rods 636 and 639. Similarly, the outfeed servo mechanism assembly 500 is operably connected to the outfeed assembly 430 via rod(s) 510.

As shown in FIG. 5, a magazine wheel rod 636 operably connects the infeed servo assembly 600 to the infeed assembly 230, by communicating rotational motion of the servo-driven motors to the infeed magazine wheel 235. Wheel hub 237 contains a cylinder, which is operably connected to the wheel rod 636, such that when the servo rotates the rod 636, the magazine wheel is rotated in the same direction. As shown in FIG. 6, the infeed servo mechanism assembly 600 is also operably connected to the infeed assembly 230 via rods 639, which are operably connected to part orienters that orient the cryocanes 50 to a proper labeling position. Similarly, the outfeed servo mechanism assembly 500 is operably connected to its corresponding outfeed assembly 430 via rod(s) 510, which are configured to move the outfeed wheels (one for each lane of cryocanes) in the outfeed assembly 430 (see FIG. 8). The singulator assembly 700 singulates the cryocanes for placement onto the lanes 350, and once the cryocanes 50 have been oriented, singulated and placed on the lanes 350, they are ready to be transported along the length of the lanes.

Accordingly, the machine is configured to receive the cryocanes 50 via an opening in the first cryogenic freezer assembly 200, which comprises a tank 201, a lid 218, an opening/port in the lid, which is sealably closeable with opening/port lid 220, which is hingeably connected to the freezer lid 219. Similarly, the machine is configured to dispense the cryocanes 50 via an opening in the second cryogenic freezer assembly 400, which comprises a tank 401, a lid 418, an opening/port in the lid, which is sealably closeable with opening/port lid 420, which is hingeably connected to the freezer lid 419. The machine is further configured such that the received cryocanes are loaded into an infeed hopper 234, at the bottom of which is situated a magazine or star wheel 235, which receives the cryocanes 50. The magazine wheel 235 is rotated by servo rod 636 to transport the cryocanes to be oriented.

In order for the machine to accurately and efficiently label products (including ampoules/vials), canes are ideally oriented with the tabs of the cane pointing towards the output side of the machine. Within the hopper 234 of the infeed assembly 230, a servo driven star wheel 235 rotates (see e.g.

Figure 11:
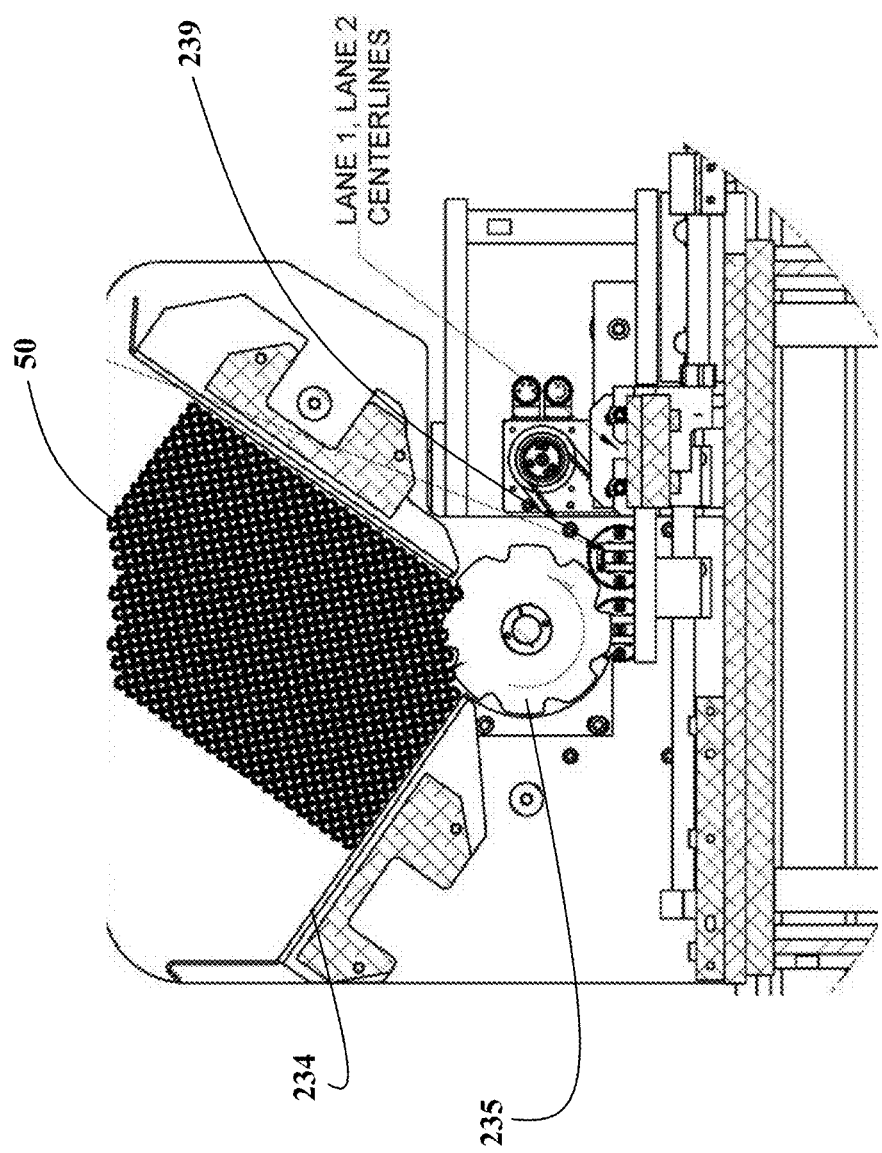
FIG. 11 is an enlarged section of the infeed assembly 230, emphasizing the magazine/star wheel/indexer 235, the orientation grippers 239, and a plurality of canes 50 loaded into the infeed hopper 234.
Figure 12:
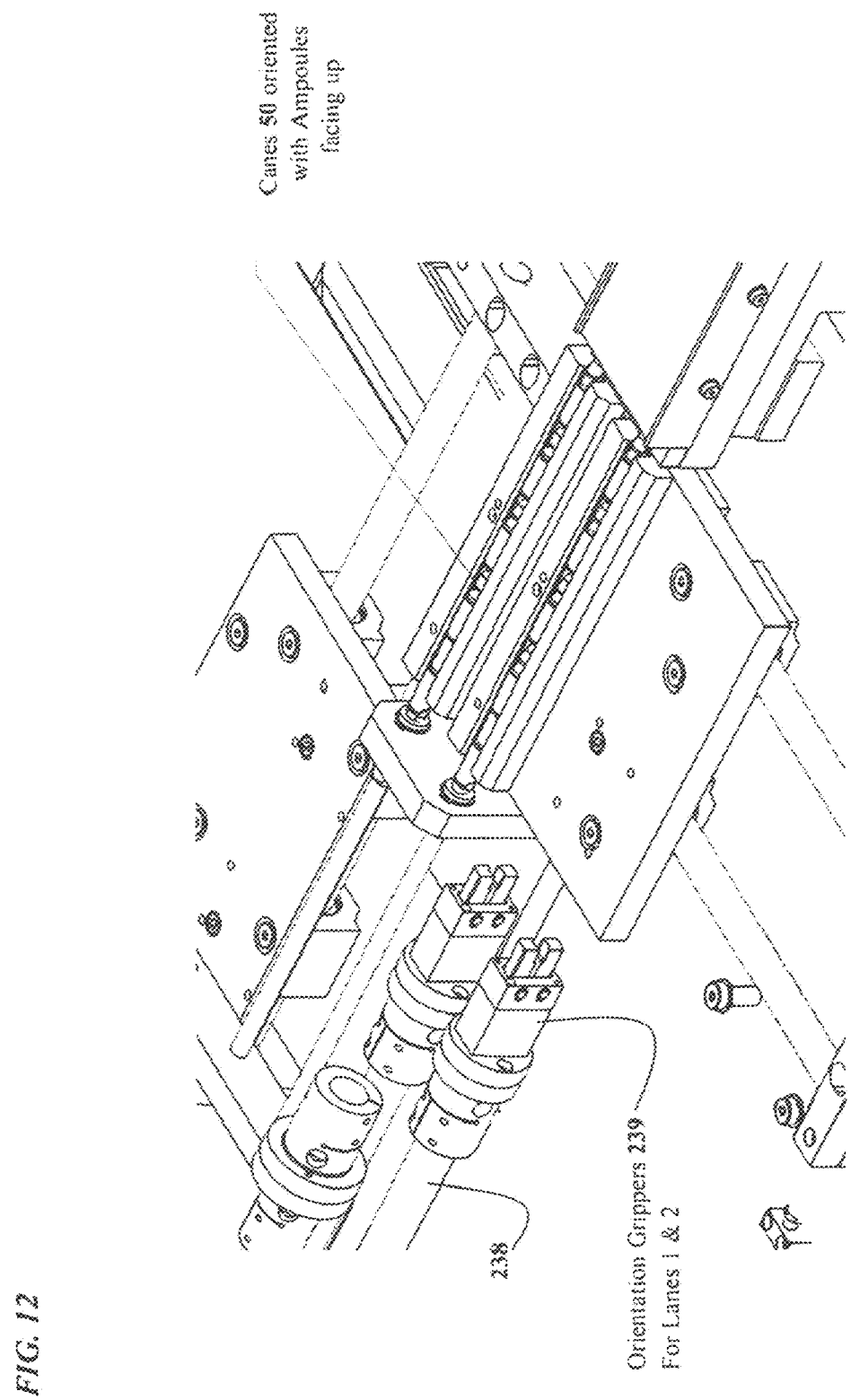
FIG. 12 is an enlarged section of the infeed assembly 230, showing the oriented canes 50 after they have been shifted to the machine's centerline.
Figure 12:
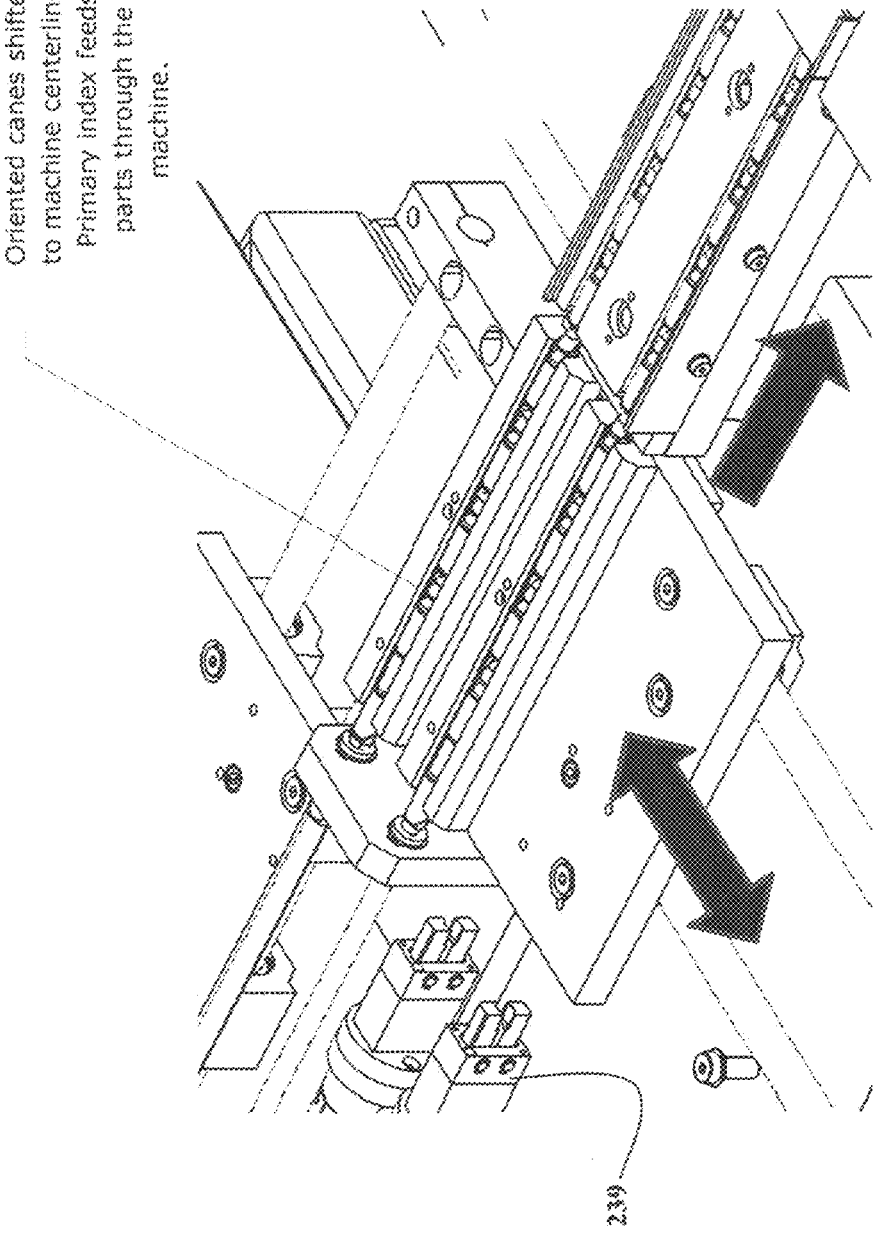

FIG. 11) counterclockwise to strip individual canes from the bottom of the hopper 234. Using routine variation, a clockwise direction could also be employed in the practice of the invention. Canes are then separated into two lanes, and, oriented radially by independent servo-controlled orientation grippers 239, such that the blank labels are properly positioned for the laser ablation step. The orientation gripper servo cylinders 238 operably connect the orientation gripper servos 237 with the orientation grippers 239. These grippers are configured to reversibly engage with (i.e. grip), radially move (i.e. rotate) and release the canes. Once oriented by the grippers 239, the canes 50 are shifted to the machine's centerline, and the primary index continues to feed parts through the machine (FIG. 12).

The oriented cryocanes are thus placed onto the lanes 350, and the infeed servo assembly 600 actuates rod 641 back and forth to sequentially advance newly arriving cryocanes down the lanes. In this manner, the newly arriving, oriented cryocanes push the earlier arrived cryocanes 50, and so on. Repeating this process, the machine sequentially moves the cryocanes 50 into the tunnel 300, determines whether the cryocanes are properly oriented using data collected from cameras 312, moves the labeled cryocanes to a position beneath quality control-checking cameras 312, determines whether the vials have been properly labeled, moves the cryocanes 50 from the tunnel 300, through the bellow joint 470, into the outfeed assembly 430, and finally, via the outfeed assembly wheels 435, out of the machine.

As shown in FIGS. 13A to 13C, lasers are placed outside of the cryogenic environment on independent positioners. Relative to the print centerline of the ampoules, the lasers can be moved rotationally (FIG. 13C) as well as horizontally and vertically. Additionally, the lasers can be moved in and out (FIG. 13B), relative to the target (e.g. blank label), for precise focal length adjustment. This movement flexibility, coupled with standard software adjustments, allows for full control over print quality and positional adjustments to match the upper and lower halves of the printed text on individual canes/ampoules. Now that the invention has been disclosed, the skilled person can envision any number of ways that the lasers may be moved in the indicated directions. For example, the lasers may be moved via the action of PLC-controlled servos, as disclosed herein.

Figure 14:
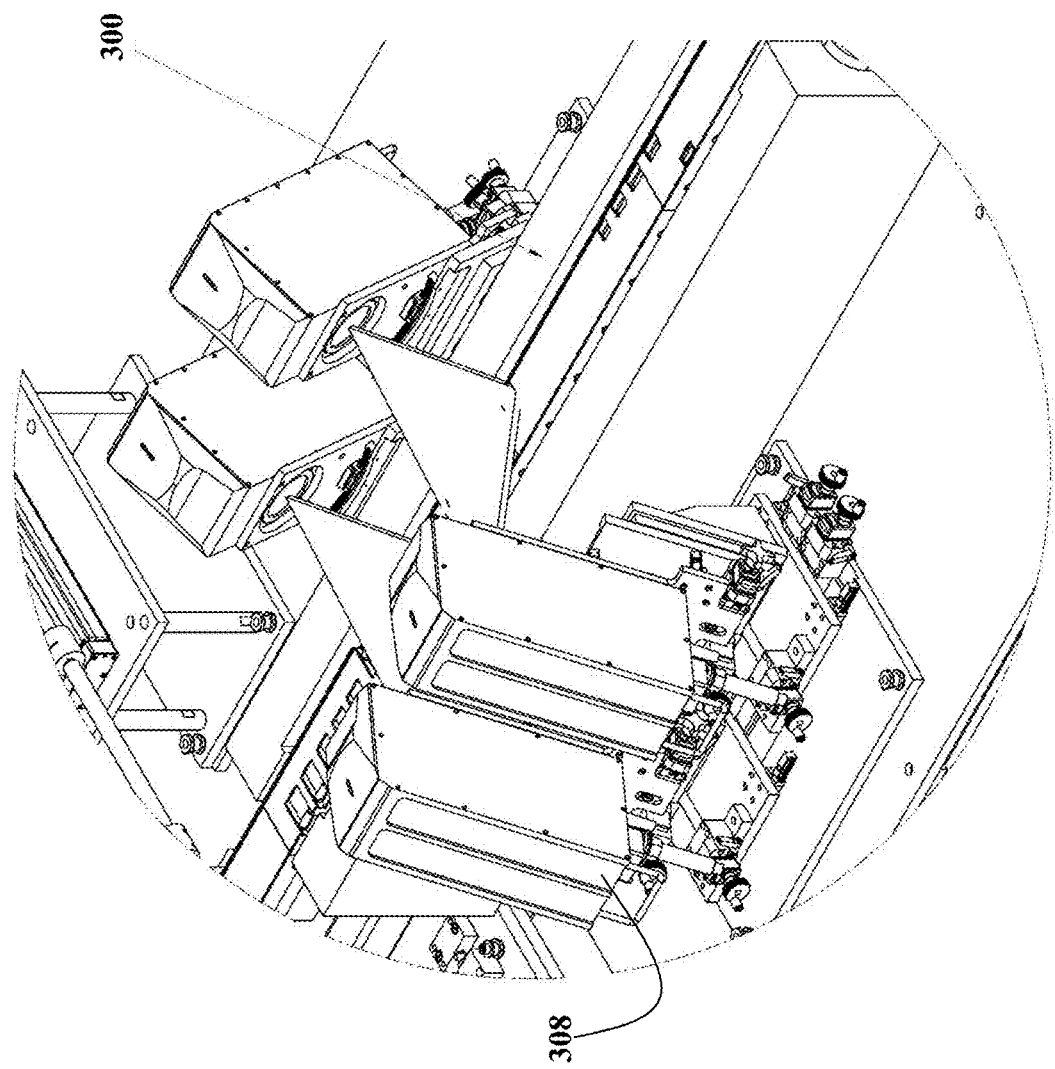
FIG. 14 shows the lasers as typically mounted onto the machine of the present disclosure.

In some embodiments, two sets of tandem laser assemblies 308 are mounted onto the machine as shown in FIG. 14. The tunnel 300 is open during machine operation and maintains the product (e.g. cryocanes with ampoules) in $LN_2$ vapor.

Figure 15A:
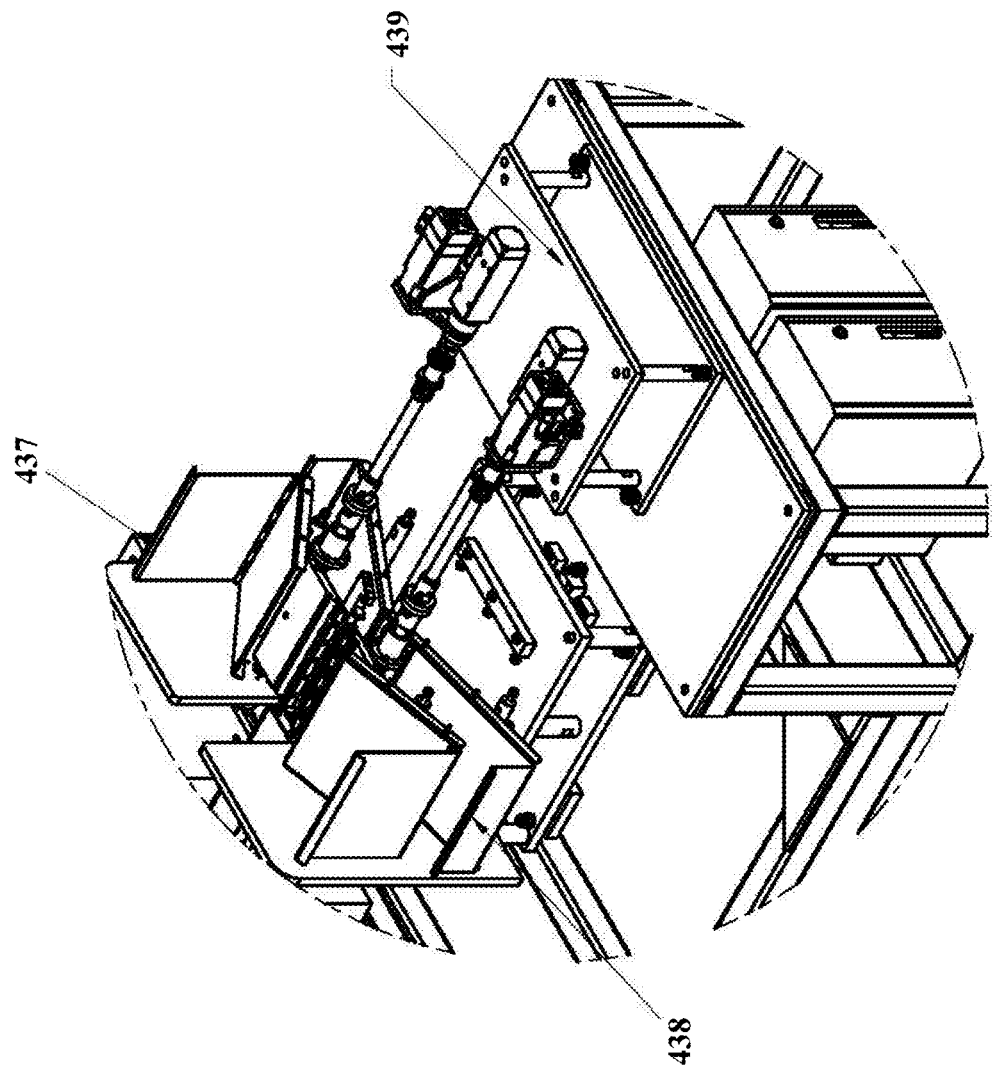
FIG. 15A is an internal view of the outfeed assembly 430, emphasizing an outfeed bin upper location 437 (for good/acceptable parts 51), an outfeed bin lower location 438 (for bad/unacceptable parts 52) and an outfeed drive unit 439. The drive unit comprises servo-controlled diverters, which divert good parts 51 to the upper location 437 and bad parts 52 to the lower location 438.
Figure 15B:
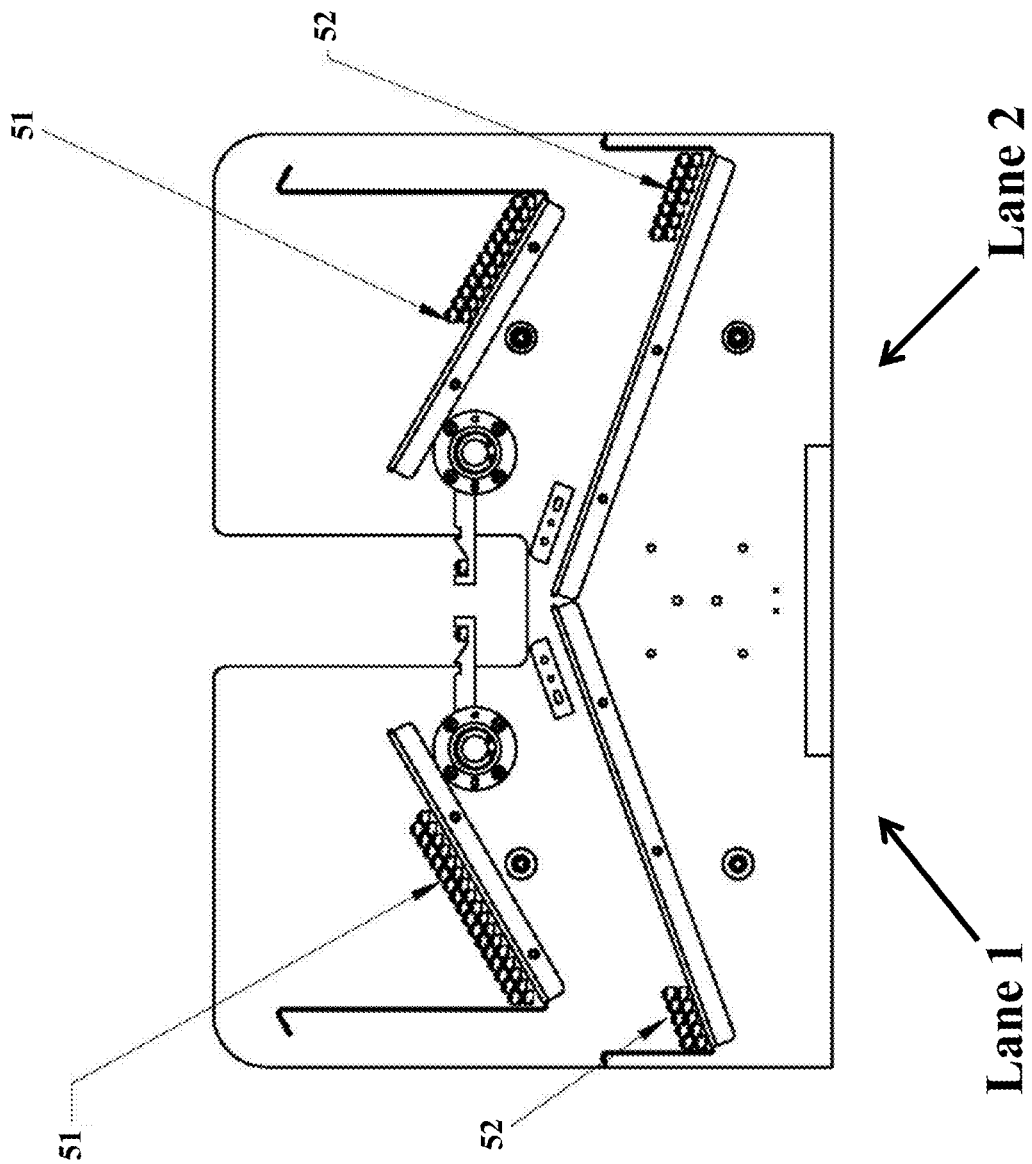
FIG. 15B is a cross-sectional view of the outfeed bin upper 437 and lower 438 locations, holding good parts 51 and bad parts 52, respectively.

As the machine indexes, canes are processed through to the outfeed assembly (FIG. 15A). After passing through the laser marking section, they are presented to an array of vision cameras. These systems examine the canes for presence of a laser mark, presence of ampoules, etc. This inspection determines if a given cane is good or bad. Canes will then exit the index bridge and enter the outfeed bin. This outfeed bin has dual servo controlled diverters for each machine lane. Based on previous good/bad results, the diverters will either lift each cane up to present it to the upper bin 437 (Good Parts 51), or drop it down to the lower bin 438 (Bad Parts 52). The machine continues to cycle until parts have been exhausted from the infeed bin and processed through to the outfeed bin(s). Once this cycle is complete, the machine can be stopped and the processed parts removed from the outfeed bins (FIG. 15B) and placed into cryo-carts.

Method of Using the Cryogenic Laser Ablation Machine

The laser ablation machine is used to apply laser marking (datalase) cryogenically-frozen vials to which had previously been applied a "blank label" (i.e. a laser-light sensitive material). Initially, a plurality of blank labeled vials 40 are filled with heat-labile biological materials, placed into cryocanes 50 and frozen to between about −150° C. to about −200° C. Thereafter, the cryocanes 50 containing the frozen vials 40 are loaded into the machine via an infeed assembly 230, which comprises a magazine wheel 235 for receiving the vials and conveying the vials to lanes 350 for subsequent transport through the machine. The vials are then properly oriented for labeling, singulated, and moved onto the lanes 350. The main index servo rod 641 then pushes a pushing plate 643, which pushes the cryocane pushing rods 644 to move the cryocanes 50 sequentially through the machine, from infeed assembly 230 to the cryostatic tunnel 300, through the tunnel 300, and into the outfeed assembly 430.

Once the vials 40 are moved into the tunnel 300 underneath the cameras 312 and laser assemblies 308, the vials 40 are labeled, provided that their orientation is determined to be acceptable. After the vials 40 are labeled, the pushing rod 641 is actuated to move the cryocanes 40 farther down the lanes 350, where they are visualized by vision assemblies 314, which comprise one or a plurality of cameras 312. If the vials 40 are determined to be properly labeled, the rod 641 will again actuate to move the cryocanes 50 down the lanes and into the outfeed assembly 430. Here, the cryocanes are unloaded via the outfeed magazines.

The invention will now be described by the following set of non-limiting claims.

What is claimed:

1. A laser ablation machine for labeling cryogenically-frozen vials, while preserving the biological efficacy of the material contained within, which comprises:
    an infeed assembly, contained within a first cryogenic freezer assembly, and configured to receive the cryogenic vials;
    a cryostatic labeling tunnel, comprising an entrance opening and an exit opening; wherein the tunnel configured to be equipped with at least one laser for labeling the vials;
    an outfeed assembly, contained within a second cryogenic freezer assembly, and configured to dispense labeled vials;
    a vial orienting means, for orienting the vials into a labeling position;
    a vial pushing means, for pushing the vials sequentially from the infeed assembly to and through the cryostatic tunnel, and from the tunnel to the outfeed assembly;
    at least one lane, beginning within the first freezer assembly, continuing through the tunnel, and ending within the second freezer assembly; wherein the at least one lane is configured to serve as a guide for the vials as they are pushed through the machine;
    a master control system, for controlling the functions of the machine;
    optionally a programmable user interface, which communicates with the master control system, for enabling a user/operator to operate the machine in a completely or partially automated manner; and
    optionally a quality control means for determining whether the vials are positioned and labeled properly.

2. The machine of claim 1, wherein the first cryogenic freezer assembly comprises an opening, through which a means for actuating the infeed assembly may pass; and, wherein the second cryogenic freezer assembly comprises an opening, through which a means for actuating the outfeed assembly may pass.

3. The machine of claim 1, wherein the first cryogenic freezer assembly comprises a first opening, through which a means for actuating the infeed assembly may pass, a second opening, through which a means for singulating the vials may pass, and a third opening, configured to connect to the beginning of the tunnel; and, wherein the second cryogenic freezer assembly comprises a first opening, through which a means for actuating the outfeed assembly may pass, and a second opening, configured to connect to the end of the tunnel.

4. The machine of claim 1, wherein each cryogenic freezer assembly comprises a freezer assembly lid, hingeably connected thereto;

wherein each freezer assembly lid comprises an access port, through which vials may be loaded or unloaded into the machine; and wherein each access port is selectably closable with an access port lid, each port lid hingeably connected to its respective freezer assembly lid.

5. The machine of claim 1, wherein the infeed assembly comprises a servo-driven infeed magazine wheel, configured to receive cryocanes holding a plurality of vials to be labeled.

6. The machine of claim 1, which comprises a means for maintaining the vials at a temperature that preserves the integrity of their contents from the time the vials enter the machine to the time when labeled vials exit the machine.

7. The machine of claim 6, wherein the means for maintaining the vials at the integrity-preserving temperature is a system that maintains a supply and level of liquid nitrogen sufficient to maintain the required temperature; and optionally, wherein the temperature maintaining means is configured to receive a supply of liquid nitrogen from an external source.

8. The machine of claim 7, comprising at least one temperature sensor, which is in operable communication with the programmable user interface, which is configured to allow a user/operator to select a maximum and minimum allowable operating temperature for the machine.

9. The machine of claim 8, wherein the machine comprises at least three temperature sensors, one contained within the first freezer assembly, a second sensor contained within the cryostatic tunnel, and a third sensor contained within the second freezer assembly.

10. A method for labeling cryogenically-frozen vials using the machine of claim 1, comprising the steps of:

providing a plurality of cryocanes, containing a plurality of blank-labeled vials, containing heat-labile biological materials;

loading the cryocanes into the infeed assembly;

singulating the cryocanes;

orienting the cryocanes to present the vials' blank labels upward;

moving the cryocanes to a position beneath the lasers; and labeling the vials with the lasers, thereby labeling the cryogenically-frozen vials.

11. The method of claim 10, further comprising the step of using a first or second camera, which are in operable connection with the programmable user interface, to determine whether the cryocanes have been oriented such that the blank-labeled vials are properly positioned beneath the lasers.

12. The method of claim 11, wherein if the cryocanes are determined to be improperly positioned, a signal is generated, communicated to the machine's user/operator and/or optionally stored within the programmable user interface.

13. The method of claim 10, further comprising the step of using a first and/or second vision assembly, which are in operable communication with the programmable user interface, to determine whether the vials have been properly labeled by the lasers.

14. The method of claim 13, wherein if the vials are determined to be improperly labeled, a signal containing details of this improper labeling is generated, communicated to the machine's user/operator and/or optionally stored within the programmable user interface.

15. The method of claim 11, further comprising the step of using a first and/or second vision assembly, which are in operable communication with the programmable user interface, to determine whether the vials have been properly labeled by the lasers.

16. The method of claim 15, wherein if the cryocanes are determined to be improperly positioned and/or the vials improperly labeled, a signal is generated to communicate this improper positioning and/or labeling information to either the user/operator, the programmable user interface, or both.

17. The method of claim 15, further comprising the step of increasing the speed of the labeling process if the cryocanes have been determined to be properly oriented and the vials have been determined to be properly labeled.

18. The method of claim 15, further comprising the step of decreasing the speed of the labeling process, or stopping the labeling process, if the cryocanes have been determined to be improperly positioned and/or improperly labeled.

19. The method of claim 18, further comprising the step of accessing the interior of the cryostatic tunnel to reposition an improperly positioned cryocane, or, to remove an improperly labeled vial.

* * * * *